United States Patent
Desai et al.

(10) Patent No.: US 12,109,203 B2
(45) Date of Patent: Oct. 8, 2024

(54) SUBSTITUTED OXAZOLIDINONES FOR THE TREATMENT OF MAMMALIAN INFECTIONS

(71) Applicant: CADILA HEALTHCARE LIMITED, Gujarat (IN)

(72) Inventors: Ranjit Desai, Gujarat (IN); Vrajesh Pandya, Gujarat (IN); Mehul Pujara, Gujarat (IN); Anil Argade, Gujarat (IN); Jignesh Joshi, Gujarat (IN); Anshul Satyanand, Gujarat (IN)

(73) Assignee: ZYDUS LIFESCIENCES LIMITED, Gujarat (IN)

( * ) Notice: Subject to any disclaimer, the term of this patent is extended or adjusted under 35 U.S.C. 154(b) by 760 days.

(21) Appl. No.: 17/262,278

(22) PCT Filed: Jul. 24, 2019

(86) PCT No.: PCT/IB2019/056322
§ 371 (c)(1),
(2) Date: Jan. 22, 2021

(87) PCT Pub. No.: WO2020/021468
PCT Pub. Date: Jan. 30, 2020

(65) Prior Publication Data
US 2021/0267953 A1     Sep. 2, 2021

(30) Foreign Application Priority Data
Jul. 25, 2018  (IN)  .............. 201821027940

(51) Int. Cl.
| | | |
|---|---|---|
| *A61K 31/438* | (2006.01) |
| *A61K 31/133* | (2006.01) |
| *A61K 31/4409* | (2006.01) |
| *A61K 31/454* | (2006.01) |
| *A61K 31/496* | (2006.01) |
| *A61K 31/4965* | (2006.01) |
| *A61K 31/5383* | (2006.01) |
| *A61K 31/606* | (2006.01) |
| *A61K 31/7036* | (2006.01) |
| *A61P 31/04* | (2006.01) |
| *C07D 413/14* | (2006.01) |
| *C07D 491/107* | (2006.01) |
| *C07D 495/10* | (2006.01) |

(52) U.S. Cl.
CPC .......... *A61K 31/438* (2013.01); *A61K 31/133* (2013.01); *A61K 31/4409* (2013.01); *A61K 31/454* (2013.01); *A61K 31/496* (2013.01); *A61K 31/4965* (2013.01); *A61K 31/5383* (2013.01); *A61K 31/606* (2013.01); *A61K 31/7036* (2013.01); *A61P 31/04* (2018.01); *C07D 413/14* (2013.01); *C07D 491/107* (2013.01); *C07D 495/10* (2013.01)

(58) Field of Classification Search
None
See application file for complete search history.

(56) References Cited

U.S. PATENT DOCUMENTS

| | | | |
|---|---|---|---|
| 7,582,659 B2 | 9/2009 | Fukuda | |
| 7,687,627 B2 * | 3/2010 | Deshpande | .......... C07D 513/10 546/19 |
| 9,988,406 B2 | 6/2018 | Reichenbacher et al. | |
| 2004/0259806 A1 * | 12/2004 | Kolobov | ................ A61K 38/05 514/1.1 |

FOREIGN PATENT DOCUMENTS

| | | |
|---|---|---|
| WO | 199525106 A1 | 9/1995 |
| WO | 2007023507 A3 | 3/2007 |
| WO | 2017015106 A1 | 1/2017 |

OTHER PUBLICATIONS

International Search Report; International Application No. PCT/IB2019/056322; International Filing Date—Jul. 24, 2019; Date of Mailing—Oct. 29, 2019; four pages.

Written Opinion; International Application No. PCT/IB2019/056322; International Filing Date—Jul. 24, 2019; Date of Mailing—Oct. 29, 2019; five pages.

\* cited by examiner

*Primary Examiner* — Dale R Miller
(74) *Attorney, Agent, or Firm* — CANTOR COLBURN LLP

(57) ABSTRACT

Present invention relates to novel compound of formula (I), their enantiomers, their diastereomers, their pharmaceutically accepted salts, or pro-drugs thereof, which are useful for the treatment of bacterial infection.

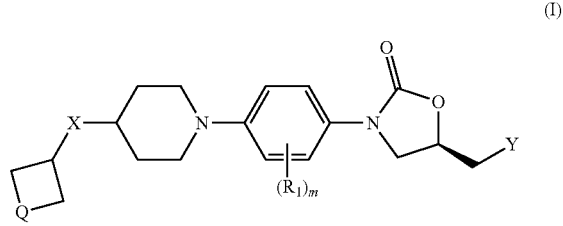

6 Claims, No Drawings

SUBSTITUTED OXAZOLIDINONES FOR THE TREATMENT OF MAMMALIAN INFECTIONS

CROSS REFERENCE TO RELATED APPLICATIONS

This application is a National Stage application of PCT/IB2019/056322, filed Jul. 24, 2019, which claims priority to Indian Application No. 201821027940, filed Jul. 25, 2018, each of which is incorporated by reference in its entirety.

FIELD OF INVENTION

The present invention relates to novel compounds of the formula (I), their tautomeric forms, their stereoisomers, their pharmaceutically acceptable salts, pharmaceutical compositions containing them, methods for their preparation. These compounds show activity against *Mycobacterium tuberculosis* infection.

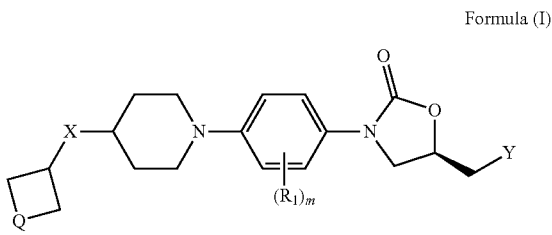

Formula (I)

BACKGROUND OF THE INVENTION

Tuberculosis (TB) is one of the leading cause of human death from infectious disease in the world. About 33% of world's population is thought to be infected with *Mycobacterium tuberculosis* (Mtb), the pathogen that causes TB disease (WHO "Global Tuberculosis Report 2016", World Health Organization, 2017). Current treatment has a potential to cure drug-sensitive TB, however treatment of drug-resistant or multi drug-resistant TB (MDR-TB) is challenging and needs a two years of combination chemotherapy (WHO "Multidrug-Resistant Tuberculosis (MDR-TB) 2016 Update", World Health Organization, 2016). Resistance to current treatment for MDR-TB and extensively resistant TB (XDR-TB) highlights the need of new drugs with novel mechanism of actions.

Linezolid is approved antibiotic for gram positive bacterial infections. It has also shown anti-bacterial activity against *Mycobacterium tuberculosis* pathogens. Linezolid and other oxazolidinone class of agents inhibit bacterial protein synthesis by binding to the peptidyl transferase center of the 50S ribosomal subunit and interfering with the placement of the aminoacyl-tRNA. They do not bind to mammalian cytoplasmic ribosomes, but do bind to mitochondrial ribosomes which are responsible for bone marrow toxicity associated with Linezolid and other oxazolidinones. Treatment of TB is lengthy which makes Linezolid not suitable for its treatment. Hence, novel oxazolidinones with improves safety profile is required which can be utilized for the treatment of TB. WO 2017015106 describes substituted phenyl oxazolidinones for the treatment of tuberculosis. KR 101271224 describes oxazolidinone derivatives containing bicyclic group having antibacterial activity against gram positive bacteria including various resistant strains. WO 2005054234 describes novel substituted piperidino phenyloxazolidinone derivatives as active ingredients and methods of treating bacterial infection. The other documents that describe oxazolidone class of inhibitors including, WO 9323384, WO 2002080841, WO 2001042242, WO 2003064415, WO 2009020616, WO 2017070024, WO 2005054234, WO 2002051819, WO 2017156519, WO 2013044865, and WO 2006059221 are also disclosed.

SUMMARY OF THE INVENTION

The present invention discloses novel compounds of the formula (I). The compounds of the present invention are useful in the treatment of the human or animal body, by regulation of bacterial protein synthesis. The compounds of this invention are therefore suitable for the treatment of tuberculosis or *Mycobacterium* infection.

EMBODIMENTS OF THE INVENTION

The main objective of the present invention is to provide novel compounds of formula (I), their tautomeric forms, novel intermediates involved in their synthesis, their pharmaceutically acceptable salts, their pharmaceutically acceptable solvates and pharmaceutical compositions containing them or their mixtures suitable for the treatment of tuberculosis or *Mycobacterium* infection.

In another embodiment is provided pharmaceutical compositions containing compounds of general formula (I), their tautomeric forms, their pharmaceutically acceptable salts, solvates and their mixtures having pharmaceutically acceptable carriers, solvents, diluents, excipients and other media normally employed in their manufacture.

In a further another embodiment is provided the use of the novel compounds of the present invention for the treatment of mammalian infections such as tuberculosis, by administering a therapeutically effective & non-toxic amount of the compound of formula (I), or their pharmaceutically acceptable compositions to the mammals.

In yet another embodiment is provided a method of treatment of the mammalian infection such as tuberculosis using compound of formula (I) or their pharmaceutically acceptable compositions to the mammals.

In final embodiment is provided a pharmaceutical composition comprising the compound of formula (I) and second therapeutic agent for the treatment of mammalian infections such as tuberculosis.

DESCRIPTION OF THE INVENTION

Accordingly, the present invention relates to compounds of the formula (I),

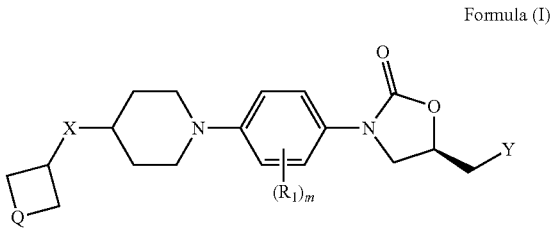

Formula (I)

Wherein,

X is either absent or a bond; whenever X is absent, four membered ring is directly attached to the 6-membered piperidine ring forming spirocyclic system;

Q is either 0 or $S(O)_p$; p=0-2 integer;

Y represents OH, $NR_2R_3$, $NHC(O)R_4$;

$R_1$ is selected from H, F, Cl, $CH_3$, CN and $OCH_3$; m=1-4 integer;

$R_2$ and $R_3$ is independently selected from H, $(C_1-C_6)$alkyl, $(C_3-C_6)$cycloalkyl, aryl, heterocyclyl and heteroaryl each of which may be further optionally substituted; $R_2$ and $R_3$ taken together with the nitrogen to which they are attached may form a 4- to 8-membered heterocyclyl or heteroaryl with 1 to 3 additional heteroatoms selected from O, S, or N and may be further be optionally substituted;

$R_4$ is independently selected from $(C_1-C_6)$alkyl, $(C_3-C_6)$cycloalkyl, aryl, heteroaryl and $(C_1-C_6)$alkoxy each of which may be further optionally substituted;

In an embodiment, when any of the $(C_1-C_6)$alkyl, $(C_3-C_6)$cycloalkyl, aryl, heterocyclyl and heteroaryl groups are optionally substituted, the groups are selected from halo, hydroxyl, $(C_1-C_6)$alkyl, $(C_1-C_6)$alkoxy, $(C_1-C_6)$acyloxy, haloalkyl, $NO_2$, CN and $NH_2$;

In a further embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;

the "alkoxy" group used either alone or in combination with other radicals, denotes a linear or branched radical containing one to six carbon attached to oxygen atom, selected from Methoxy, ethoxy, n-propoxy, iso-propoxy, n-butoxy, sec-butoxy, iso-butoxy, pentyloxy, hexyloxy and the like;

the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like;

the "haloalkyl" group is selected from an alkyl radical, as defined above, suitably substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;

the "heterocyclyl" or "heterocyclic" group used either alone or in combination with other radicals, is selected from suitable saturated, partially saturated or unsaturated aromatic or non-aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, az aquinazolinoyl, thienopyrimidonyl, quinazolonyl, pyrimidonyl, benzoxazinyl, benzoxazinonyl, benzothiazinyl, benzothiazinonyl, thieno piperidinyl, and the like; In one embodiment, the heterocycle group, wherever applicable, may consists of appropriate number of carbon atoms and include from 1-4 heteroatoms selected from the group consisting of N, O, and $S(O)_p$, p=0-2;

the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the "aralkyl" group used either alone or in combination with other radicals, is selected from groups containing an aryl radical, as defined above, attached directly to an alkyl radical, as define above, more preferably groups selected from benzyl, phenethyl, and the like;

the "heterocyclylalkyl" group used either alone or in combination with other radicals, is selected from groups containing an heterocyclyl radical, as defined above, attached directly to an alkyl radical, as define above;

the "spirocyclic system" is a group wherein one cyclic ring is attached to another cyclic ring via one carbon atom that is common carbon atom to both cyclic ring.

Further preferred embodiments are those disclosed below.

Preferred "$(C_1-C_6)$alkyl" group of $R_2$, $R_3$ and $R_4$ is selected from methyl, ethyl, n-propyl, iso-propyl;

Preferred "$(C_1-C_6)$alkoxy" group of $R_2$, $R_3$ and $R_4$ is selected from methoxy and ethoxy;

Preferred "$(C_3-C_6)$cycloalkyl" group of $R_2$, $R_3$ and $R_4$ is selected from cyclopropyl and cyclobutyl;

Preferred "heteroaryl" group of $R_2$ and $R_3$ is selected from triazolyl, isoxazolyl, thienyl, furyl.

Suitable groups and substituents on the groups may be selected from those described anywhere in the specification.

Preferred compounds according to the present invention include but are not limited to:

(R)-5-((1H-1,2,3-triazol-1-yl)methyl)-3-(4-(2,2-dioxido-2-thia-7-azaspiro[3.5]nonan-7-yl)-3,5-difluorophenyl)oxazolidin-2-one;

(S)-3-(4-(2,2-dioxido-2-thia-7-azaspiro[3.5]nonan-7-yl)-3,5-difluorophenyl)-5-((isoxazol-3-ylamino)methy)oxazolidin-2-one;

(S)—N-((3-(4-(2,2-dioxido-2-thia-7-azaspiro[3.5]nonan-7-yl)-3,5-difluorophenyl)-2-oxooxazolidin-5-yl)methyl)acetamide;

(S)-methyl ((3-(4-(2,2-dioxido-2-thia-7-azaspiro[3.5] nonan-7-yl)-3,5-difluorophenyl)-2-oxooxazolidin-5-yl) methyl)carbamate;

(S)—N-((3-(4-(2,2-dioxido-2-thia-7-azaspiro[3.5]nonan-7-yl)-3-fluorophenyl)-2-oxooxazolidin-5-yl)methyl)acetamide;
(S)—N-((3-(3,5-difluoro-4-(2-oxa-7-azaspiro[3.5]nonan-7-yl)phenyl)-2-oxooxazolidin-5-yl)methyl)acetamide;
(S)—N-((3-(3-fluoro-4-(2-oxa-7-azaspiro[3.5]nonan-7-yl)phenyl)-2-oxooxazolidin-5-yl)methyl)acetamide;
(S)—N-((3-(3,5-difluoro-4-(4-(oxetan-3-yl)piperidin-1-yl)phenyl)-2-oxooxazolidin-5-yl)methyl)acetamide;
(S)—N-((3-(4-(4-(1,1-dioxidothietan-3-yl)piperidin-1-yl)-3,5-difluorophenyl)-2-oxooxazolidin-5-yl)methyl)acetamide;
(S)—N-((3-(4-(4-(1,1-dioxidothietan-3-yl)piperidin-1-yl)-3-fluorophenyl)-2-oxooxazolidin-5-yl)methyl)acetamide;
methyl (S)-((3-(4-(4-(1,1-dioxidothietan-3-yl)piperidin-1-yl)-3,5-difluorophenyl)-2-oxooxazolidin-5-yl)methyl)carbamate;
(S)-5-(aminomethyl)-3-(4-(4-(1,1-dioxidothietan-3-yl)piperidin-1-yl)-3,5-difluorophenyl)oxazolidin-2-one;
(R)-3-(4-(4-(1,1-dioxidothietan-3-yl)piperidin-1-yl)-3,5-difluorophenyl)-5-(hydroxymethyl)oxazolidin-2-one;
(S)-5-(aminomethyl)-3-(3,5-difluoro-4-(4-(oxetan-3-yl)piperidin-1-yl)phenyl)oxazolidin-2-one;
(S)-5-(aminomethyl)-3-(3,5-difluoro-4-(2-oxa-7-azaspiro[3.5]nonan-7-yl)phenyl)oxazolidin-2-one;
(S)-5-(aminomethyl)-3-(4-(2,2-dioxido-2-thia-7-azaspiro[3.5]nonan-7-yl)-3,5-difluorophenyl)oxazolidin-2-one;
(R)-3-(4-(2,2-dioxido-2-thia-7-azaspiro[3.5]nonan-7-yl)-3,5-difluorophenyl)-5-(hydroxymethyl)oxazolidin-2-one;
(S)—N-((3-(4-(2,2-dioxido-2-thia-7-azaspiro[3.5]nonan-7-yl)-3,5-difluorophenyl)-2-oxooxazolidin-5-yl)methyl)thiophene-2-carboxamide;
(S)—N-((3-(4-(2,2-dioxido-2-thia-7-azaspiro[3.5]nonan-7-yl)-3-fluorophenyl)-2-oxooxazolidin-5-yl)methyl)thiophene-2-carboxamide;
(S)—N-((3-(4-(2,2-dioxido-2-thia-7-azaspiro[3.5]nonan-7-yl)-3,5-difluorophenyl)-2-oxooxazolidin-5-yl)methyl)furan-2-carboxamide;
(S)—N-((3-(4-(2,2-dioxido-2-thia-7-azaspiro[3.5]nonan-7-yl)-3-fluorophenyl)-2-oxooxazolidin-5-yl)methyl)furan-2-carboxamide;
(S)—N-((3-(4-(4-(1,1-dioxidothietan-3-yl)piperidin-1-yl)-3,5-difluorophenyl)-2-oxooxazolidin-5-yl)methyl)thiophene-2-carboxamide;
(S)—N-((3-(4-(4-(1,1-dioxidothietan-3-yl)piperidin-1-yl)-3-fluorophenyl)-2-oxooxazolidin-5-yl)methyl)thiophene-2-carboxamide;
(S)—N-((3-(4-(4-(1,1-dioxidothietan-3-yl)piperidin-1-yl)-3,5-difluorophenyl)-2-oxooxazolidin-5-yl)methyl)furan-2-carboxamide;
(S)—N-((3-(4-(4-(1,1-dioxidothietan-3-yl)piperidin-1-yl)-3-fluorophenyl)-2-oxooxazolidin-5-yl)methyl)furan-2-carboxamide;
(S)—N-((3-(4-(2,2-dioxido-2-thia-7-azaspiro[3.5]nonan-7-yl)-3,5-difluorophenyl)-2-oxooxazolidin-5-yl)methyl)butyramide;
(S)—N-((3-(4-(2,2-dioxido-2-thia-7-azaspiro[3.5]nonan-7-yl)-3-fluorophenyl)-2-oxooxazolidin-5-yl)methyl)butyramide;
(S)—N-((3-(4-(4-(1,1-dioxidothietan-3-yl)piperidin-1-yl)-3,5-difluorophenyl)-2-oxooxazolidin-5-yl)methyl)butyramide;
(S)—N-((3-(4-(4-(1,1-dioxidothietan-3-yl)piperidin-1-yl)-3-fluorophenyl)-2-oxooxazolidin-5-yl)methyl)butyramide;
ethyl (S)-((3-(4-(2,2-dioxido-2-thia-7-azaspiro[3.5]nonan-7-yl)-3,5-difluorophenyl)-2-oxooxazolidin-5-yl)methyl)carbamate;
ethyl (S)-((3-(4-(2,2-dioxido-2-thia-7-azaspiro[3.5]nonan-7-yl)-3-fluorophenyl)-2-oxooxazolidin-5-yl)methyl)carbamate;
ethyl (S)-((3-(4-(4-(1,1-dioxidothietan-3-yl)piperidin-1-yl)-3,5-difluorophenyl)-2-oxooxazolidin-5-yl)methyl)carbamate;
ethyl (S)-((3-(4-(4-(1,1-dioxidothietan-3-yl)piperidin-1-yl)-3-fluorophenyl)-2-oxooxazolidin-5-yl)methyl)carbamate;
(S)—N-((3-(4-(2,2-dioxido-2-thia-7-azaspiro[3.5]nonan-7-yl)-3,5-difluorophenyl)-2-oxooxazolidin-5-yl)methyl)cyclopropanecarboxamide;
(S)—N-((3-(4-(2,2-dioxido-2-thia-7-azaspiro[3.5]nonan-7-yl)-3-fluorophenyl)-2-oxooxazolidin-5-yl)methyl)cyclopropanecarboxamide;
(S)—N-((3-(4-(4-(1,1-dioxidothietan-3-yl)piperidin-1-yl)-3,5-difluorophenyl)-2-oxooxazolidin-5-yl)methyl)cyclopropanecarboxamide;
(S)—N-((3-(4-(4-(1,1-dioxidothietan-3-yl)piperidin-1-yl)-3-fluorophenyl)-2-oxooxazolidin-5-yl)methyl)cyclopropanecarboxamide;
(S)—N-((3-(4-(2,2-dioxido-2-thia-7-azaspiro[3.5]nonan-7-yl)-3,5-difluorophenyl)-2-oxooxazolidin-5-yl)methyl)cyclobutanecarboxamide;
(S)—N-((3-(4-(2,2-dioxido-2-thia-7-azaspiro[3.5]nonan-7-yl)-3-fluorophenyl)-2-oxooxazolidin-5-yl)methyl)cyclobutanecarboxamide;
(S)—N-((3-(4-(4-(1,1-dioxidothietan-3-yl)piperidin-1-yl)-3,5-difluorophenyl)-2-oxooxazolidin-5-yl)methyl)cyclobutanecarboxamide;
(S)—N-((3-(4-(4-(1,1-dioxidothietan-3-yl)piperidin-1-yl)-3-fluorophenyl)-2-oxooxazolidin-5-yl)methyl)cyclobutanecarboxamide;
(R)-5-((1H-1,2,3-triazol-1-yl)methyl)-3-(4-(2,2-dioxido-2-thia-7-azaspiro[3.5]nonan-7-yl)-3-fluorophenyl)oxazolidin-2-one;
(R)-5-((1H-1,2,3-triazol-1-yl)methyl)-3-(4-(4-(1,1-dioxidothietan-3-yl)piperidin-1-yl)-3,5-difluorophenyl)oxazolidin-2-one;
(R)-5-((1H-1,2,3-triazol-1-yl)methyl)-3-(4-(4-(1,1-dioxidothietan-3-yl)piperidin-1-yl)-3-fluorophenyl)oxazolidin-2-one;
(R)-5-((1H-1,2,4-triazol-1-yl)methyl)-3-(4-(2,2-dioxido-2-thia-7-azaspiro[3.5]nonan-7-yl)-3,5-difluorophenyl)oxazolidin-2-one;
(R)-5-((1H-1,2,4-triazol-1-yl)methyl)-3-(4-(2,2-dioxido-2-thia-7-azaspiro[3.5]nonan-7-yl)-3-fluorophenyl)oxazolidin-2-one;
(S)-3-(4-(2,2-dioxido-2-thia-7-azaspiro[3.5]nonan-7-yl)-3-fluorophenyl)-5-((isoxazol-3-ylamino)methyl)oxazolidin-2-one;
(S)-3-(4-(4-(1,1-dioxidothietan-3-yl)piperidin-1-yl)-3,5-difluorophenyl)-5-((isoxazol-3-ylamino)methyl)oxazolidin-2-one;
methyl (S)-((3-(4-(4-(1,1-dioxidothietan-3-yl)piperidin-1-yl)-3-fluorophenyl)-2-oxooxazolidin-5-yl)methyl)carbamate;
methyl (S)-((3-(4-(2,2-dioxido-2-thia-7-azaspiro[3.5]nonan-7-yl)-3-fluorophenyl)-2-oxooxazolidin-5-yl)methyl)carbamate;
methyl (S)-((3-(3-fluoro-4-(2-oxa-7-azaspiro[3.5]nonan-7-yl)phenyl)-2-oxooxazolidin-5-yl)methyl)carbamate;
(R)-54(1H-1,2,3-triazol-1-yl)methyl)-3-(3-fluoro-4-(2-oxa-7-azaspiro[3.5]nonan-7-yl)phenyl)oxazolidin-2-one;

methyl (S)-((3-(3,5-difluoro-4-(2-oxa-7-azaspiro[3.5]nonan-7-yl)phenyl)-2-oxooxazolidin-5-yl)methyl)carbamate;

(R)-54(1H-1,2,3-triazol-1-yl)methyl)-3-(3,5-difluoro-4-(2-oxa-7-azaspiro[3.5]nonan-7-yl)phenyl)oxazolidin-2-one;

(R)-54(1H-1,2,3-triazol-1-yl)methyl)-3-(3,5-difluoro-4-(4-(oxetan-3-yl)piperidin-1-yl)phenyl)oxazolidin-2-one.

The novel compounds of this invention may be prepared using the reactions and techniques as shown in scheme below and described in this section. The reactions are performed in solvents appropriate to the reagents and materials employed and are suitable for the transformations being affected. It is understood by those skilled in the art that the nature and order of the synthetic steps presented may be varied for the purpose of optimizing the formation of the compounds of the present invention. It will also be well appreciated that one or more of the reactants may be protected and de-protected for facile synthesis by techniques known to persons skilled in the art. It will also be appreciated that one or more of the compounds of the present invention may exist in stereoisomeric and/or diastereomeric forms. Such stereoisomers and/or diastereoisomers as well as their optical antipodes are to be construed to be within the scope of the present invention. It will also be well appreciated that one or more of these compounds may be converted to their salts and other derivatives based on the specific groups present on the compounds, which can be well comprehended by persons skilled in the art. Such salts and/or other derivatives, as the case may be should also be construed to be within the scope of the present invention.

Scheme 1: Synthesis of compounds of general formula (I)

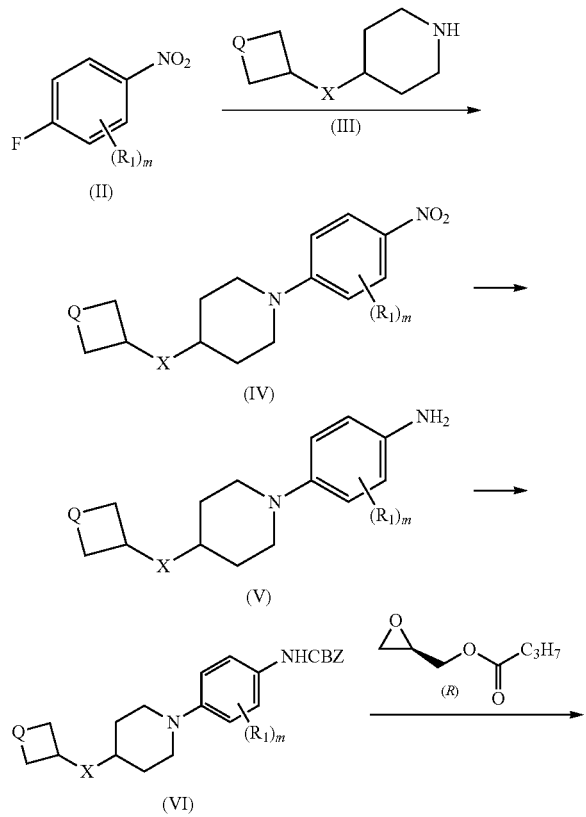

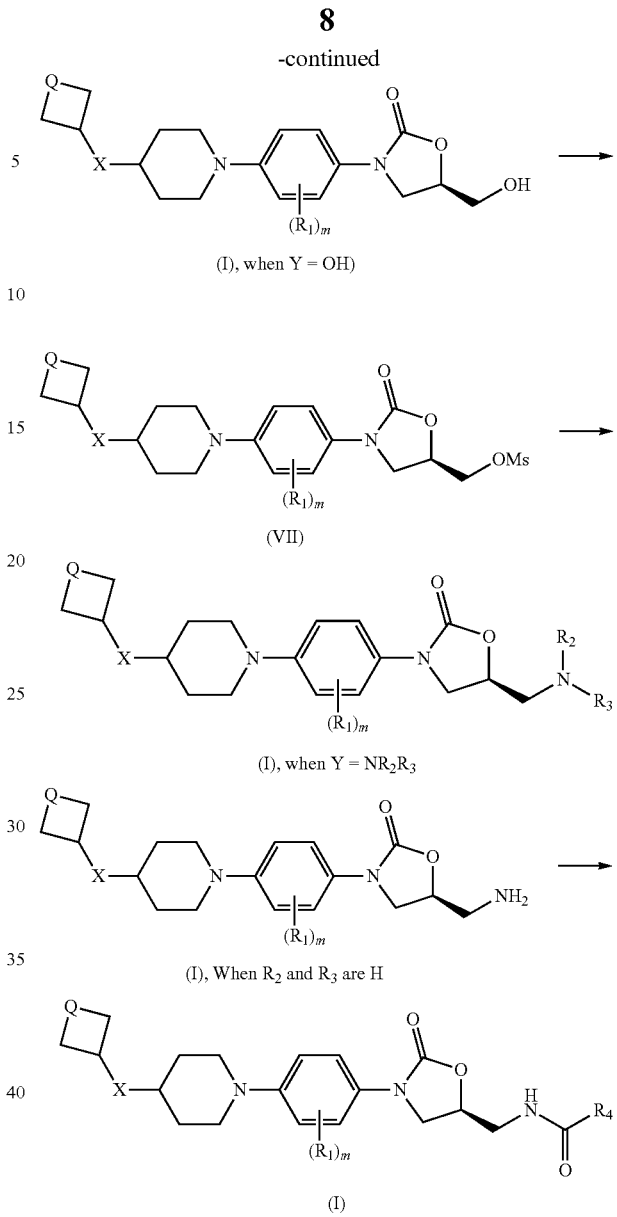

The compound (IV) can be obtained by reacting compounds of the formula (II) with (III) in the presence of base such as sodium carbonate, $K_2CO_3$, sodium hydride etc. in solvents such as THF, DMF, MeOH etc. The compounds of general formula (V) can be obtained by reduction using stannous chloride dihydrate in ethyl acetate. The compounds of the general formula (VI) can be obtained by reacting (V) with benzyl oxy carbonyl chloride using sodium carbonate as a base in solvents such as water ethyl acetate, acetonitrile or mixture thereof. Compounds of the formula (I, when Y=OH) can be obtained by treating it with n-butyl lithium and R-glycidyl butyrate in THF. It was then converted into mesylate derivatives (VII) using methane sulfonyl chloride and TEA in solvents such as THF, ACN etc., which was then reacted with appropriately substituted amines to get desired compounds (I, when Y=$NR_2R_3$). Compounds (I, when Y=$NH_2$) are further reacted with appropriate acid chloride or anhydride in presence of base such as TEA or pyridine to get compounds of the formula (I) with amide or carbamate linkage.

Scheme 2: Synthesis of compounds of general formula (I)

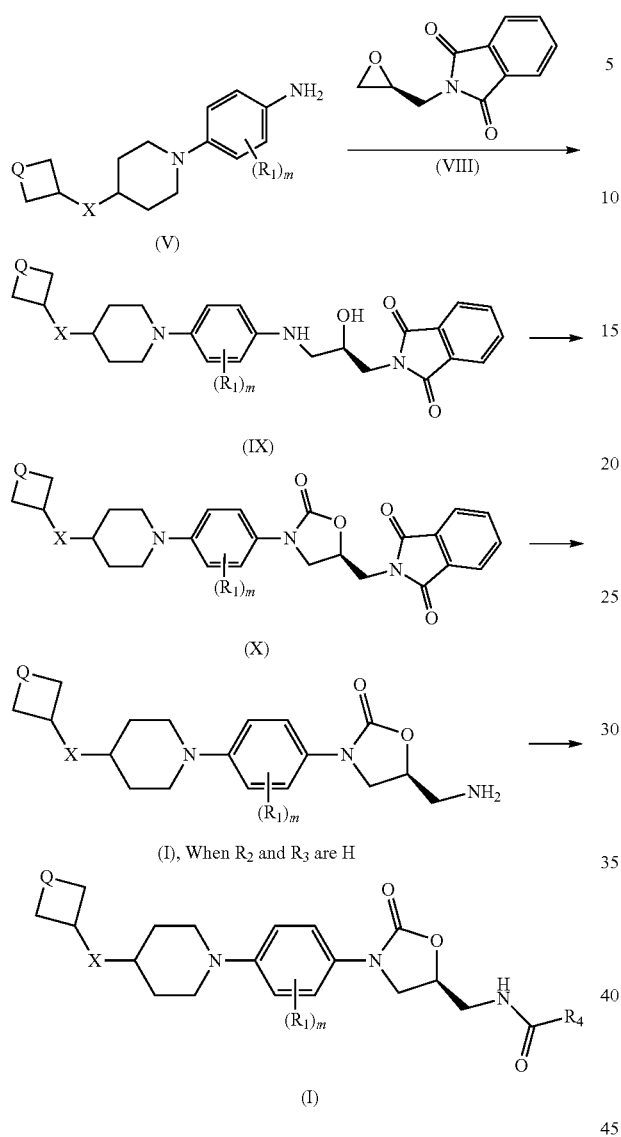

(I), When R₂ and R₃ are H

Alternatively compound of the general formula (V) can be reacted with compounds of the formula (VIII) (prepared according to the procedure described in Tetrahedron: Asymmetry, 7(6), 1641-1648; 1996) in solvents such as MeOH, EtOH etc. to get compounds (IX). The compounds of general formula (X) can be obtained by cyclisation of (X) with CDI in solvent such as DCM, CHCl₃ etc. The compounds (I) (when Y=NH₂) are obtained by deprotection of phthalimide group using aq. Methyl amine in protic solvents such as MeOH, EtOH etc. Compounds (I, when Y=NH₂) are further reacted with appropriate acid chloride or anhydride in presence of base such as TEA or pyridine to get compounds of the formula (I) with amide or carbamate linkage.

List of Abbreviations
  ACN: Acetonitrile
  CDI: 1,1'-Carbonyldiimidazole
  CHCl₃: Chloroform
  DCM: Dichloromethane
  DMAP: 4-dimethylaminopyridine
  DMF: Dimethylformamide
  DMSO: Dimethyl sulfoxide
  EtOAc: Ethyl acetate
  EtOH: Ethanol
  K₂CO₃: Potassium Carbonate
  LiAlH₄: Lithium Aluminium hydride
  MeOH: Methanol
  NaHCO₃: Sodium bicarbonate
  Na₂SO₄: Sodium sulfate
  NaOH: Sodium hydroxide
  Pd-C: Palladium Charcoal
  TEA: Triethylamine
  TFA: Trifluoroacetic acid
  THF: Tetrahydrofuran
  ¹H NMR: Proton Nuclear Magnetic Resonance
  h: Hour(s)
  min: Minute(s)
  J: Coupling constant in units of Hz
  Hz: Hertz
  MABA: Microplate Alamar Blue Assay Preparation of Compounds Example 1

Preparation of (R)-5-((1H-1,2,3-triazol-1-yl)methyl)-3-(4-(2,2-dioxido-2-thia-7-azaspiro[3.5]nonan-7-yl)-3,5-difluorophenyl)oxazolidin-2-one

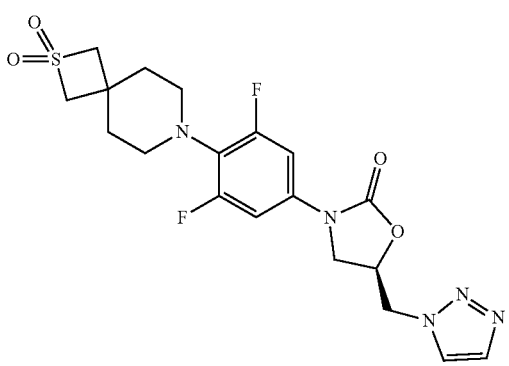 [SMILES: O=C1O[C@@H](Cn2ccnn2)CN1c1cc(F)c(N2CCC3(CC2)CS(=O)(=O)C3)c(F)c1]

Step 1:
N-benzyl-2-chloro-N-(2-chloroethyl)ethan-1-amine

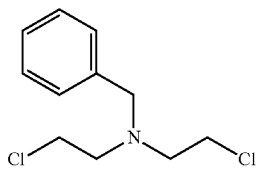 [SMILES: ClCCN(CCCl)Cc1ccccc1]

Bis(2-chloroethyl)amine (208 g, 1462 mmol) was added to DCM (200 ml) followed by 2M NaOH solution and stirred for 30 min. at 25-30° C. Separate DCM layer dry over Na₂SO₄ and evaporate to get oil (free amine) To this was added ACN (500 mL) followed by benzyl bromide (69.5 ml, 585 mmol) and K₂CO₃ (242 g, 1754 mmol) at 25-30° C. and stirred for 16 h at 80° C. Reaction mixture was filtered and filtrate was evaporated to get crude oil which was purified by column chromatography using Hexane/EtOAc. ESI-MS (m/z): 232.05 [M+H]$^+$.

Step 2: diethyl 1-benzylpiperidine-4,4-dicarboxylate

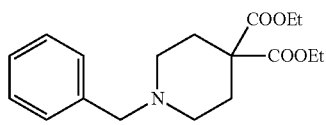 [SMILES: CCOC(=O)C1(C(=O)OCC)CCN(Cc2ccccc2)CC1]

To a stirring solution of product of step 1 (17 g, 73.2 mmol) in DMF was added $K_2CO_3$ (30.4 g, 220 mmol), diethyl malonate (11.17 ml, 73.2 mmol) and tetrabutylammonium bromide (2.361 g, 7.32 mmol) at 25-30° C. Reaction mixture was stirred for 16 h at 90° C. After completion of reaction, it was diluted with EtOAc and washed with water. EtOAc layer was dried over $Na_2SO_4$ and evaporated to get crude product which was purified by column chromatography using Hexane/EtOAc. ESI-MS (m/z): 320.22 [M+H]$^+$.

Step 3: (1-benzylpiperidine-4,4-diyl)dimethanol

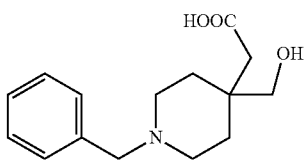 [SMILES: O=C(O)CC1(CO)CCN(Cc2ccccc2)CC1]

To a stirring solution of product of step 2 (26 g, 81 mmol) in THF was added $LiAlH_4$ (9.27 g, 244 mmol) at 0° C. and stirred it for 16 h at 25-30° C. After completion of reaction, it was cooled to 0° C. and diluted with 10 ml of water followed by 10 ml of 10% aq. NaOH solution and filtered over Hyflow bed. Residue was washed with 10% MeOH in EtOAc. Filtrate was evaporated to get the title product. ESI-MS (m/z): 236.15 [M+H]$^+$.

Step 4: piperidine-4,4-diyldimethanol

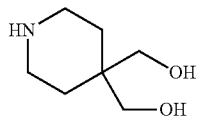

To a stirring solution of product of step 3 (4.50 g, 19.12 mmol) in MeOH was added Pd-C (0.407 g, 3.82 mmol) followed by ammonium formate (3.62 g, 57.4 mmol). Reaction mixture was refluxed for 6 h. After completion of reaction, mixture was passed through hyflow bed and washed with 20% MeOH in EtOAc. Organic layer was distilled out to get the title product. ESI-MS (m/z): 146.10 [M+H]$^+$.

Step 5: tert-butyl 4,4-bis(hydroxymethyl)piperidine-1-carboxylate

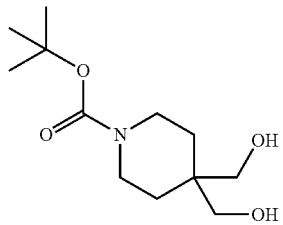 [SMILES: CC(C)(C)OC(=O)N1CCC(CO)(CO)CC1]

To a stirring solution of product of step 4 (9.4 g, 64.7 mmol) in DMF was added TEA (13.54 ml, 97 mmol) and Di-tert-butyl dicarbonate (15.03 ml, 64.7 mmol). Reaction mixture was stirred for 3 h at 25-30° C. After completion of reaction, reaction mixture was diluted with EtOAc (150 ml) and washed with water (30 ml). Organic layer was distilled out to get the title product.

Step 6: tert-butyl 4,4-bis(((methylsulfonyl)oxy)methyl)piperidine-1-carboxylate

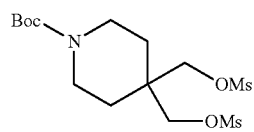

To a stirring solution of product of step 5 (10 g, 40.8 mmol) in DCM was added TEA (22.92 ml, 163 mmol) followed by methanesulfonyl chloride (9.46 ml, 122 mmol) at 0-5° C. and reaction mixture was stirred for 2 h at 25-30° C. After completion of reaction it was diluted with DCM (50 ml) and water (25 ml). Organic layer was separated, dried over $Na_2SO_4$, and concentrated under reduced pressure to get the title product.

Step 7: tert-butyl 2-thia-7-azaspiro[3.5]nonane-7-carboxylate

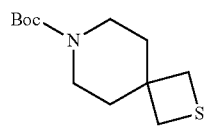

To a stirring solution of product of step 6 (4.90 g, 12.20 mmol) in EtOH was added Sodium sulfide nonahydrate (3.52 g, 14.65 mmol) and reaction mixture was refluxed for 16 h. After completion of reaction it was diluted with EtOAc (100 mL). Organic layer was separated, dried over $Na_2SO_4$ and evaporated to get crude product which was purified by column chromatography using Hexane/EtOAc to get the title product.

Step 8: tert-butyl 2-thia-7-azaspiro[3.5]nonane-7-carboxylate 2,2-dioxide

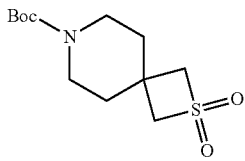 [SMILES: CC(C)(C)OC(=O)N1CCC2(CC1)CS(=O)(=O)C2]

In a round-bottomed flask oxone (9.60 g, 15.61 mmol) in water (45 mL) was added at 0-5° C. To this was added product of step 7 (1.90 g, 7.81 mmol) dissolved in MeOH dropwise at 0-5° C. The reaction mixture was stirred at 15-20° C. for 4 h. The reaction mixture was filtered and washed with MeOH (30 ml). MeOH was evaporated and residue was extracted with DCM. Organic layer was dried over $Na_2SO_4$ and evaporated under reduced pressure to get title product as solid.

Step 9: 7-(2,6-difluoro-4-nitrophenyl)-2-thia-7-azaspiro[3.5]nonane 2,2-dioxide

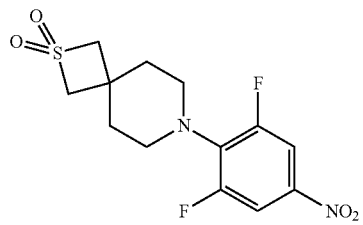 [SMILES: O=[N+]([O-])c1cc(F)c(N2CCC3(CC2)CS(=O)(=O)C3)c(F)c1]

To a stirring solution of product of step 8 (0.650 g, 2.361 mmol) in DCM was added TFA (0.903 ml, 11.80 mmol) at 0-5° C. and stirred for 3 h at 25-30° C. After completion of reaction, DCM was evaporated under reduced pressure to get the crude product which was diluted with DMF (10 mL). To this was added $K_2CO_3$ (0.946 g, 6.85 mmol) and 1,2,3-trifluoro-5-nitrobenzene (0.404 g, 2.283 mmol) and stirred for 4 h at 80° C. Reaction mixture was then diluted with water solid obtained was filtered to get the title product. ESI-MS (m/z): 333.14 $[M+H]^+$.

Step 10: 7-(4-amino-2,6-difluorophenyl)-2-thia-7-azaspiro[3.5]nonane 2,2-dioxide

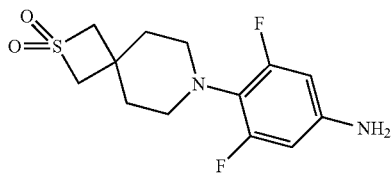 [SMILES: Nc1cc(F)c(N2CCC3(CC2)CS(=O)(=O)C3)c(F)c1]

To a stirring solution of product of step 9 (0.690 g, 2.076 mmol) in EtOAc was added Tin(II) chloride dihydrate (2.342 g, 10.38 mmol) and stirred for 1.5 h at 80° C. After completion of reaction it was cooled to 25° C. and basified by aq ammonia solution. EtOAc was decanted and residue was again extracted with EtOAc. Combined EtOAc layer was dried over $Na_2SO_4$ and concentrated to get the titled product. ESI-MS (m/z): 303.15 $[M+H]^+$.

Step 11: benzyl (4-(2,2-dioxido-2-thia-7-azaspiro[3.5]nonan-7-yl)-3,5-difluorophenyl)carbamate

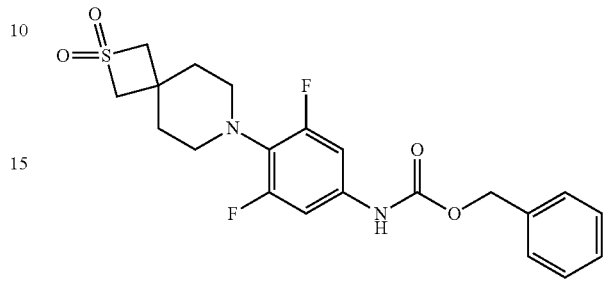

To a stirring solution of product of step 10 (0.535 g, 1.770 mmol) in THF was added $NaHCO_3$ (0.223 g, 2.65 mmol) and benzyl chloroformate (0.785 g, 2.300 mmol) at 0-5° C. The reaction mixture was stirred at 25-30° C. for 7 h. After completion of reaction it was diluted with EtOAC and water. Organic layer was separated, dried and evaporated under reduced pressure to get the crude product which was purified by column chromatography using Hexane/EtOAc to get the pure product. ESI-MS (m/z): 437.16 $[M+H]^+$.

Step 12: (R)-3-(4-(2,2-dioxido-2-thia-7-azaspiro[3.5]nonan-7-yl)-3,5-difluorophenyl)-5-(hydroxymethyl)oxazolidin-2-one

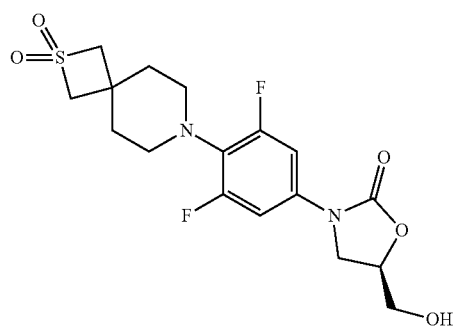 [SMILES: O=C1O[C@@H](CO)CN1c1cc(F)c(N2CCC3(CC2)CS(=O)(=O)C3)c(F)c1]

To a stirring solution of product of step 11 (830 mg, 1.902 mmol) in dry THF was added n-butyl lithium (2.282 ml (2.5 M), 5.70 mmol) at −78° C. The resultant light yellow solution was stirred at −78° C. for 1 h and then (R)-glycidyl butyrate (685 mg, 4.75 mmol) was added at −70-75° C. dropwise. The reaction mixture was stirred for an additional 1 h at −78° C. The reaction mixture was allowed to warm to room temperature and stirred for 16 h. The reaction mixture was diluted with water and EtOAc. Organic layer was separated, dried over $Na_2SO_4$, and concentrated to get crude product as oil. The crude product was purified by column chromatography to get the title product. ESI-MS (m/z): 403.14 $[M+H]^+$.

Step 13: (R)-(3-(4-(2,2-dioxido-2-thia-7-azaspiro[3.5]nonan-7-yl)-3,5-difluorophenyl)-2-oxooxazolidin-5-yl)methyl methanesulfonate

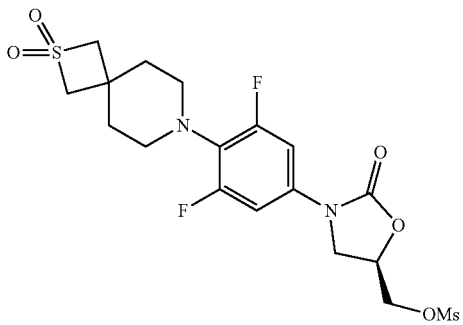 [SMILES: CS(=O)(=O)OC[C@H]1CN(c2cc(F)c(N3CCC4(CC3)CS(=O)(=O)C4)c(F)c2)C(=O)O1]

To a stirring solution of product of step 12 (220 mg, 0.547 mmol) in DCM was added TEA (0.133 ml, 0.957 mmol) and methanesulfonyl chloride (0.047 ml, 0.601 mmol) at 0-5° C. Reaction mixture was stirred for 2 h at 25-30° C. After completion of reaction it was diluted with DCM and washed with water. DCM layer was separated, dried over $Na_2SO_4$, and evaporated to get the title product. ESI-MS (m/z): 481.16 $[M+H]^+$.

Step 14: (R)-5-((1H-1,2,3-triazol-1-yl)methyl)-3-(4-(2,2-dioxido-2-thia-7-azaspiro[3.5]nonan-7-yl)-3,5-difluorophenyl)oxazolidin-2-one

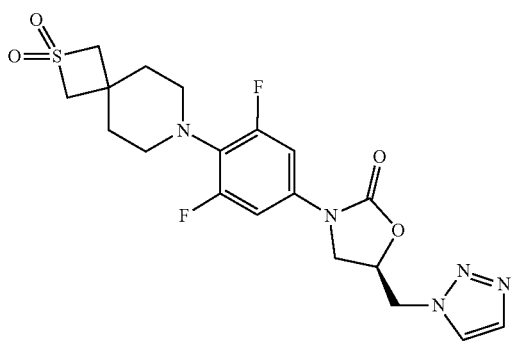 [SMILES: O=C1O[C@@H](Cn2ccnn2)CN1c1cc(F)c(N2CCC3(CC2)CS(=O)(=O)C3)c(F)c1]

To a stirring solution of product of step 13 (100 mg, 0.208 mmol) in DMF was added 1H-1,2,3-triazole (0.024 ml, 0.416 mmol) and $K_2CO_3$ (57.5 mg, 0.416 mmol). Reaction mixture was heated to 80° C. After completion of reaction it was diluted with EtOAc and water. EtOAc layer was separated, washed with water, dried over $Na_2SO_4$, and concentrated to get crude product. The crude product was purified by column chromatography to get the title product. $^1H$ NMR (DMSO-$d_6$): 8.16 (s, 1H), 7.77 (s, 1H), 7.22 (d, J=8.4 Hz, 2H), 5.23 (m, 1H), 5.17-5.11 (m, 2H), 4.83-4.81 (m, 1H), 4.21-4.17 (m, 1H), 4.03 (s, 4H), 3.87-3.84 (m, 1H), 3.01 (s, 4H), 1.95 (s, 4H). ESI-MS (m/z): 454.12 $[M+H]^+$.

Example 2

Preparation of (S)-3-(4-(2,2-dioxido-2-thia-7-azaspiro[3.5]nonan-7-yl)-3,5-difluorophenyl)-5-((isoxazol-3-ylamino)methyl)oxazolidin-2-one

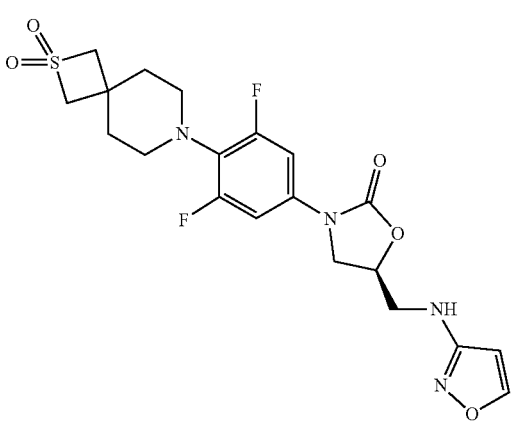 [SMILES: O=C1O[C@@H](CNc2ccon2)CN1c1cc(F)c(N2CCC3(CC2)CS(=O)(=O)C3)c(F)c1]

Step 1: (R)-tert-butyl 43-(4-(2,2-dioxido-2-thia-7-azaspiro[3.5]nonan-7-yl)-3,5-difluorophenyl)-2-oxooxazolidin-5-yl)methyl)(isoxazol-3-yl)carbamate

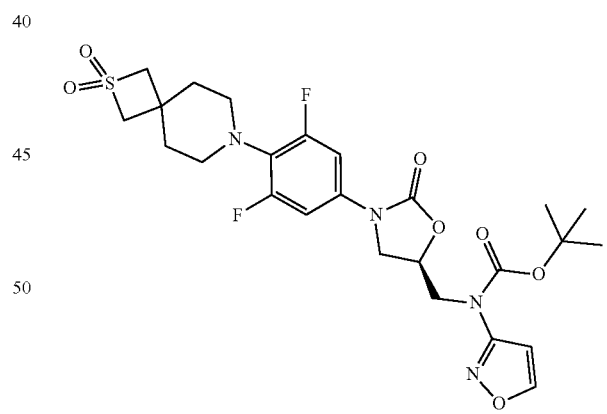

To a stirring solution of (R)-(3-(4-(2,2-dioxido-2-thia-7-azaspiro[3.5]nonan-7-yl)-3,5-difluorophenyl)-2-oxooxazolidin-5-yl)methyl methanesulfonate (100 mg, 0.208 mmol) in DMF was added tert-butyl isoxazol-3-ylcarbamate (57.5 mg, 0.312 mmol) and $K_2CO_3$ (57.5 mg, 0.416 mmol). Reaction mixture was stirred at 80° C. for 3 h. After completion of reaction it was diluted with EtOAc and water. EtOAc layer was separated, dried over $Na_2SO_4$' and concentrated to get crude product which was purified by column chromatography using EtOAc:Hexane to get the title product. ESI-MS (m/z): 569.16 $[M+H]^+$.

Step 2: (S)-3-(4-(2,2-dioxido-2-thia-7-azaspiro[3.5]nonan-7-yl)-3,5-difluorophenyl)-5-((isoxazol-3-ylamino)methy)oxazolidin-2-one

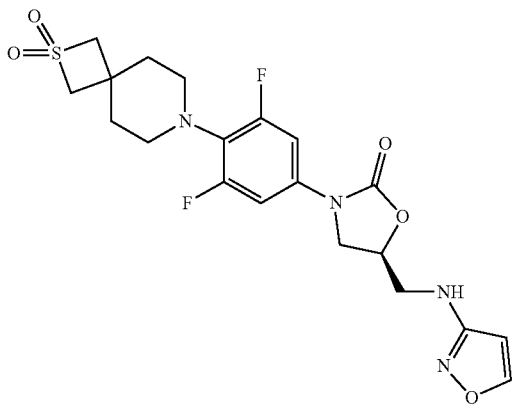 [SMILES: O=C1O[C@@H](CNc2ccon2)CN1c1cc(F)c(N2CCC3(CC2)CS(=O)(=O)C3)c(F)c1]

To a stirring solution of step 1 (70 mg, 0.123 mmol) in DCM (10 ml) was added TFA (0.047 ml, 0.616 mmol) at 0-5° C. and stirred for 2 h. After completion of reaction it was diluted with EtOAc and washed with saturated solution of NaHCO$_3$. Organic layer was separated, dried over Na$_2$SO$_4$, and concentrated to get crude product. The crude product was purified by column chromatography using EtOAc:Hexane to get the title product. $^1$H NMR (DMSO): 8.39 (d, J=1.6 Hz, 1H), 7.25 (d, J=11.6 Hz, 2H), 6.52 (t, 1H), 5.99 (d, J=2.0 Hz, 1H), 5.89 (m, 1H), 4.11 (m, 1H), 4.02 (s, 4H), 3.79-3.77 (s, 1H), 3.44-3.41 (m, 2H), 3.03-3.00 (m, 4H), 1.90-1.88 (m, 4H). ESI-MS (m/z): 469.12 [M+H]$^+$.

Example 3

Preparation of (S)—N-((3-(4-(2,2-dioxido-2-thia-7-azaspiro[3.5]nonan-7-yl)-3,5-difluorophenyl)-2-oxooxazolidin-5-yl)methy)acetamide

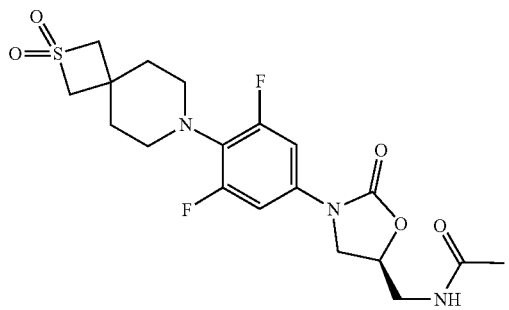 [SMILES: CC(=O)NC[C@H]1CN(c2cc(F)c(N3CCC4(CC3)CS(=O)(=O)C4)c(F)c2)C(=O)O1]

Step 1: (R)-5-(azidomethyl)-3-(4-(2,2-dioxido-2-thia-7-azaspiro[3.5]nonan-7-yl)-3,5-difluorophenyl)oxazolidin-2-one

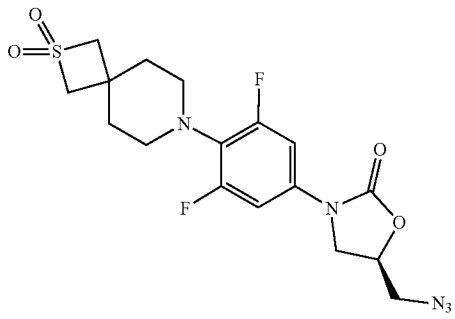 [SMILES: [N-]=[N+]=NC[C@H]1CN(c2cc(F)c(N3CCC4(CC3)CS(=O)(=O)C4)c(F)c2)C(=O)O1]

To a stirring solution of (R)-(3-(4-(2,2-dioxido-2-thia-7-azaspiro[3.5]nonan-7-yl)-3,5-difluorophenyl)-2-oxooxazolidin-5-yl)methyl methanesulfonate (380 mg, 0.791 mmol) in DMF was added sodium azide (257 mg, 3.95 mmol) and stirred for 16 h at 60-65° C. After completion of reaction it was diluted with EtOAc and water. Organic layer was separated, dried over Na$_2$SO$_4$, and concentrated to get the title product. ESI-MS (m/z): 428.05 [M+H]$^+$.

Step 2: (S)-5-(aminomethyl)-3-(4-(2,2-dioxido-2-thia-7-azaspiro[3.5]nonan-7-yl)-3,5-difluorophenyl)oxazolidin-2-one

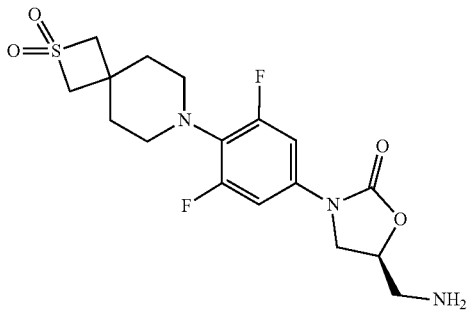 [SMILES: NC[C@H]1CN(c2cc(F)c(N3CCC4(CC3)CS(=O)(=O)C4)c(F)c2)C(=O)O1]

To a stirring solution of product of step 1 (0.330 g, 0.772 mmol) in MeOH (5 ml) was added Pd-C(0.016 g, 0.154 mmol) at 0° C. To this was added sodium borohydride (0.088 g, 2.316 mmol) portion wise and stirred for 3 h at 25-30° C. After completion of reaction it was passed through hyflow bed and washed with EtOAc (50 ml). Organic layer was dried over Na$_2$SO$_4$ and concentrated to get the title product. ESI-MS (m/z): 402.09 [M+H]$^+$.

Step 3: (S)—N-((3-(4-(2,2-dioxido-2-thia-7-azaspiro[3.5]nonan-7-yl)-3,5-difluorophenyl)-2-oxooxazolidin-5-yl)methyl)acetamide

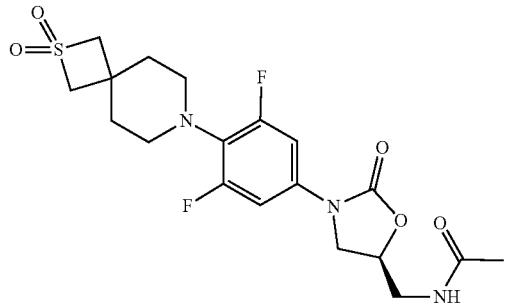 [SMILES: CC(=O)NC[C@H]1CN(c2cc(F)c(N3CCC4(CC3)CS(=O)(=O)C4)c(F)c2)C(=O)O1]

To a stirring solution of product of step 2 (150 mg, 0.374 mmol) in DCM was added pyridine (0.030 ml, 0.374 mmol) and acetic anhydride (0.035 ml, 0.374 mmol) and stirred for 3 h at 25-30° C. After completion of reaction it was diluted with water and product was extracted with DCM. Organic layer was dried over $Na_2SO_4$ and concentrated to get the crude product which was purified by column chromatography to get the title product. $^1$H NMR (DMSO-$d_6$): 8.24 (t, J=5.8 Hz, 1H), 7.23 (dd, J=5.2 and 16.8 Hz, 2H), 4.74-4.70 (m, 1H), 4.10-4.05 (m, 1H), 4.03 (s, 4H), 3.70-3.68 (m, 1H), 3.41-3.38 (m, 2H), 3.01-3.00 (m, 4H), 1.91-1.87 (m, 4H), 1.83 (s, 4H). ESI-MS (m/z): 444.20 [M+H]$^+$.

Example 4

Preparation of (S)-methyl 43-(4-(2,2-dioxido-2-thia-7-azaspiro[3.5]nonan-7-yl)-3,5-difluorophenyl)-2-oxooxazolidin-5-yl)methyl)carbamate

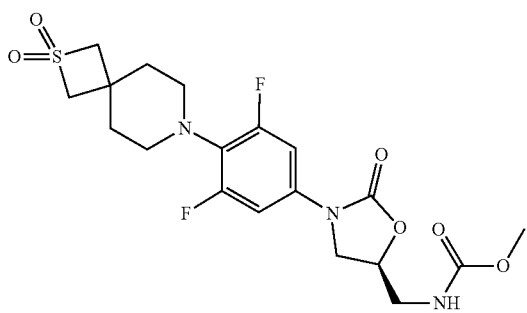 [SMILES: COC(=O)NC[C@H]1CN(c2cc(F)c(N3CCC4(CC3)CS(=O)(=O)C4)c(F)c2)C(=O)O1]

To a stirring solution of (S)-5-(aminomethyl)-3-(4-(2,2-dioxido-2-thia-7-azaspiro[3.5]nonan-7-yl)-3,5-difluorophenyl)oxazolidin-2-one (100 mg, 0.249 mmol) in DCM was added pyridine (0.030 ml, 0.374 mmol) followed by methyl chloroformate (0.023 ml, 0.299 mmol) and stirred for 3 h at 25-30° C. After completion of reaction it was diluted with water and product was extracted with DCM (20 ml). Organic layer was dried over $Na_2SO_4$ and concentrated to get the crude product which was purified by column chromatography to get the title product. $^1$H NMR (DMSO-$d_6$): 7.53 (bs, 1H), 7.24 (d, J=12 Hz, 2H), 4.73 (s, 1H), 4.10-4.06 (m, 2H), 4.02 (s, 4H), 3.741-3.61 (m, 2H), 3.40 (s, 3H), 3.19-3.13 (m, 4H), 1.89 (m, 4H). ESI-MS (m/z): 460.17 (M+H)$^+$.

Example 5

Preparation of (S)—N-((3-(4-(2,2-dioxido-2-thia-7-azaspiro[3.5]nonan-7-yl)-3-fluorophenyl)-2-oxooxazolidin-5-yl)methyl)acetamide

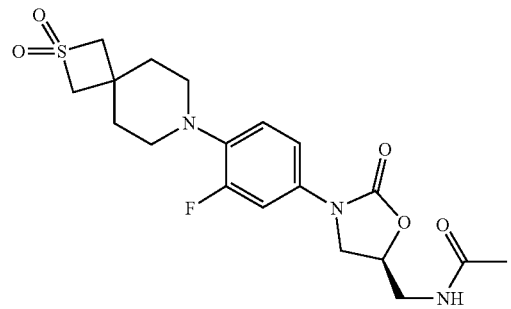 [SMILES: CC(=O)NC[C@H]1CN(c2ccc(N3CCC4(CC3)CS(=O)(=O)C4)c(F)c2)C(=O)O1]

Prepared using similar process as described for example 3. $^1$H NMR (DMSO-$d_6$): 8.24 (t, 1H), 7.49-7.45 (m, 1H), 7.18-7.16 (m, 1H), 7.07-7.03 (m, 1H), 4.72 (m, 1H), 4.10-4.05 (m, 1H), 4.02 (s, 4H), 2.94-2.91 (m, 4H), 1.95-1.92 (m, 4H), 1.24 (s, 3H). ESI-MS (m/z): 426.14 [M+H]$^+$.

Example 6

Preparation of (S)—N-((3-(3,5-difluoro-4-(2-oxa-7-azaspiro[3.5]nonan-7-yl)phenyl)-2-oxooxazolidin-5-yl)methyl)acetamide

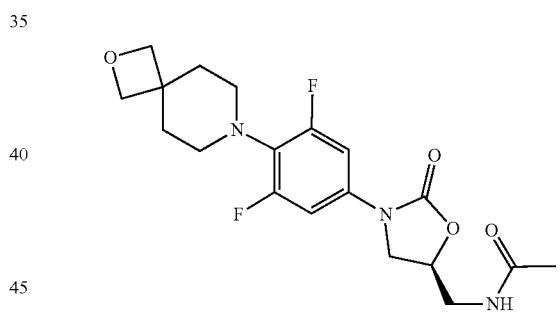

Step 1: tert-butyl 2-oxa-7-azaspiro[3.5]nonane-7-carboxylate

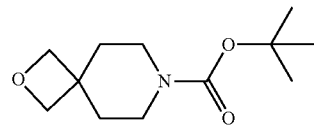 [SMILES: CC(C)(C)OC(=O)N1CCC2(CC1)COC2]

To a stirring solution of tert-butyl 4,4-bis(hydroxymethyl)piperidine-1-carboxylate (880 mg, 3.59 mmol) in THF was added n-butyllithium (1.435 ml, 3.59 mmol) dropwise at 0-5° C. The reaction mixture was stirred at 0-5° C. for 30 min. To this was added a solution of p-toluene sulfonylchloride (684 mg, 3.59 mmol) in THF dropwise at 0-5° C. The reaction mixture was stirred at 0-5° C. for 30 min. To this was added n-butyllithium (1.435 ml, 3.59 mmol) at 0-5° C.

Reaction mixture was heated at 60° C. for 2 h. RM was poured into water and product was extracted with EtOAC. Organic layer was distilled out to get crude product which was purified by column chromatography using Hexane/EtOAc to get the pure product.

Step 2: 7-(2,6-difluoro-4-nitrophenyl)-2-oxa-7-azaspiro[3.5]nonane

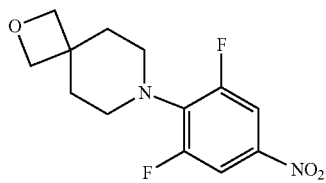 [SMILES: O=[N+]([O-])c1cc(F)c(N2CCC3(CC2)COC3)c(F)c1]

To a stirring solution of product of step 1 (840 mg, 3.70 mmol) in DCM was added TFA (1.4 ml, 18.48 mmol) at 0-5° C. and stirred for 3 h at 25-30° C. After completion of reaction, DCM was evaporated under reduced pressure to get the crude product which was diluted with DMF. To this was added $K_2CO_3$ (1.17 g, 8.47 mmol) and 1,2,3-trifluoro-5-nitrobenzene (600 mg, 3.39 mmol) and stirred for 4 h at 80° C. Reaction mixture was diluted with water to get solid product. ESI-MS (m/z): 285.08 $[M+H]^+$.

Step 3: 3,5-difluoro-4-(2-oxa-7-azaspiro[3.5]nonan-7-yl)aniline

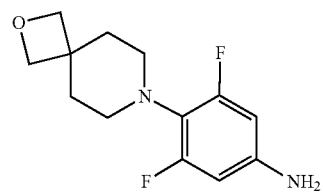 [SMILES: Nc1cc(F)c(N2CCC3(CC2)COC3)c(F)c1]

To a stirring solution of product of step 2 (720 mg, 2.53 mmol) in THF (10 ml) was added Pd-C(27 mg) and stirred under hydrogen pressure for 16 h at 25° C. After completion of reaction it was passed through hyflow bed and solvent was evaporated to get the title product. ESI-MS (m/z): 255.10 $[M+H]^+$.

Step 4: benzyl (3,5-difluoro-4-(2-oxa-7-azaspiro[3.5]nonan-7-yl)phenyl)carbamate

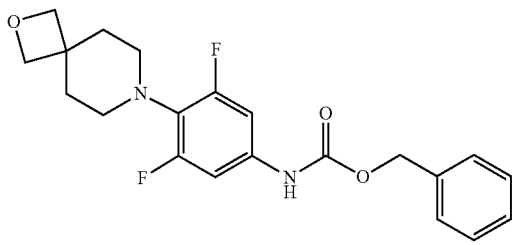 [SMILES: O=C(Nc1cc(F)c(N2CCC3(CC2)COC3)c(F)c1)OCc1ccccc1]

To a stirring solution of product of step 3 (700 mg, 2.75 mmol) in THF (10 ml) was added $NaHCO_3$ (925 mg, 11.01 mmol) and benzyl chloroformate (0.865 ml, 3.03 mmol) at 0° C. The reaction mixture was stirred at 25-30° C. for 16 h. After completion of reaction it was diluted with EtOAc and water. Organic layer was evaporated under reduced pressure to get the crude product. The crude product was purified by column chromatography using Hexane/EtOAc to get the title product. ESI-MS (m/z): 389.16 $[M+H]^+$.

Step 5: (R)-3-(3,5-difluoro-4-(2-oxa-7-azaspiro[3.5]nonan-7-yl)phenyl)-5-(hydroxymethyl)oxazolidin-2-one

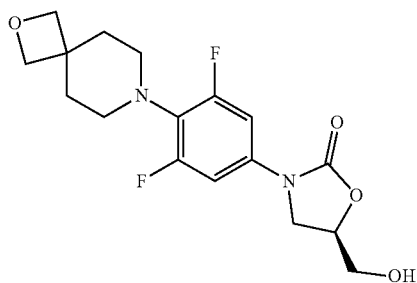 [SMILES: O=C1O[C@@H](CO)CN1c1cc(F)c(N2CCC3(CC2)COC3)c(F)c1]

To a stirring solution of product of step 4 (540 mg, 1.390 mmol) in dry THF was added n-butyllithium (0.612 ml, 1.529 mmol) at −78° C. The resultant light yellow solution was stirred at −78° C. for 1 h and then (R)-glycidyl butyrate (220 mg, 1.529 mmol) was added at −70° C. dropwise. The reaction mixture was stirred for an additional 1 h at −78° C. The reaction mixture was allowed to warm to room temperature and stirred for 16 h. After completion of reaction it was poured into aq. ammonium chloride solution and crude product was extracted with EtOAc which was purified by column chromatography to get the title product. ESI-MS (m/z): 355.14 $[M+H]^+$.

Step 6: (R)-(3-(3,5-difluoro-4-(2-oxa-7-azaspiro[3.5]nonan-7-yl)phenyl)-2-oxooxazolidin-5-yl)methyl methanesulfonate

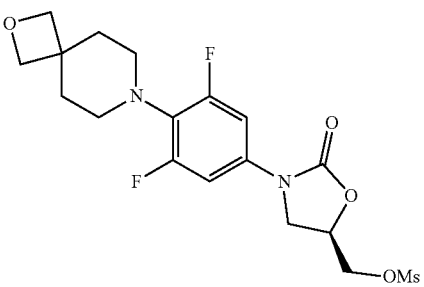 [SMILES: CS(=O)(=O)OC[C@H]1CN(c2cc(F)c(N3CCC4(CC3)COC4)c(F)c2)C(=O)O1]

To a stirring solution of product of step 5 (316 mg, 0.892 mmol) in DCM was added TEA (0.162 ml, 1.159 mmol) and methanesulfonyl chloride (0.07 ml, 0.936 mmol) at 0° C. Reaction mixture was stirred for 2 h at 25-30° C. After completion of reaction it was diluted with DCM (10 ml) and washed with water. DCM layer was dried over $Na_2SO_4$ and distilled out to get the title product. ESI-MS (m/z): 433.12 $[M+H]^+$.

Step 7: (R)-5-(azidomethyl)-3-(3,5-difluoro-4-(2-oxa-7-azaspiro[3.5]nonan-7-yl)phenyl)oxazolidin-2-one

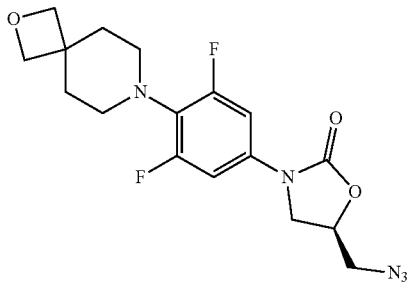 [SMILES: [N-]=[N+]=NC[C@H]1CN(c2cc(F)c(N3CCC4(CC3)COC4)c(F)c2)C(=O)O1]

To a stirring solution of product of step 6 (397 mg, 0.918 mmol) in DMF was added sodium azide (298 mg, 4.59 mmol) and stirred for 3 h at 60-65° C. After completion of reaction it was diluted with water and filtered to get the title product. ESI-MS (m/z): 380.14 [M+H]$^+$.

Step 8: (S)-5-(aminomethyl)-3-(3,5-difluoro-4-(2-oxa-7-azaspiro[3.5]nonan-7-yl)phenyl)oxazolidin-2-one

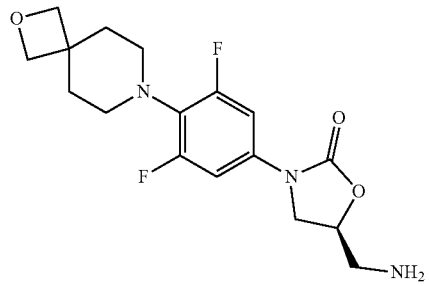 [SMILES: NC[C@H]1CN(c2cc(F)c(N3CCC4(CC3)COC4)c(F)c2)C(=O)O1]

To a stirring solution of product of step 7 (242 mg, 0.638 mmol) in MeOH was added Pd-C at 0-5° C. To this was added sodium borohydride (72.4 mg, 1.914 mmol) portion wise and stirred for 3 h at 25-30° C. After completion of reaction it was passed through hyflow bed and washed with EtOAc (20 ml). Organic layer was dried over Na$_2$SO$_4$ and concentrated to get the title product. ESI-MS (m/z): 354.15 [M+H]$^+$.

Step 9: (S)—N-((3-(3,5-difluoro-4-(2-oxa-7-azaspiro[3.5]nonan-7-yl)phenyl)-2-oxooxazolidin-5-yl)methyl)acetamide

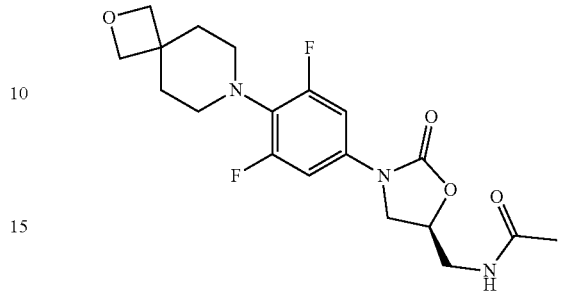

To a stirring solution of product of step 8 (100 mg, 0.283 mmol) in DCM was added pyridine (0.034 ml, 0.424 mmol) and acetic anhydride (0.037 ml, 0.396 mmol). Reaction mixture stirred for 1 h at 25-30° C. After completion of reaction it was diluted with DCM and washed with water. Organic layer was dried over Na$_2$SO$_4$ and concentrated to get the title product. $^1$H NMR (DMSO-d$_6$): 8.22 (t, J=5.8 Hz, 1H), 7.23 (d, J=11.6 Hz, 2H), 4.73-4.70 (m, 1H), 4.34 (s, 4H), 4.09-4.05 (m, 1H), 3.70-3.66 (m, 1H), 3.40-3.37 (m, 2H), 2.96-2.93 (m, 4H), 1.99-1.86 (m, 4H), 1.83 (s, 3H). ESI-MS (m/z): 396.16 (M+H)$^+$.

Example 7

Preparation of (S)—N-((3-(3-fluoro-4-(2-oxa-7-azaspiro[3.5]nonan-7-yl)phenyl)-2-oxooxazolidin-5-yl)methyl)acetamide

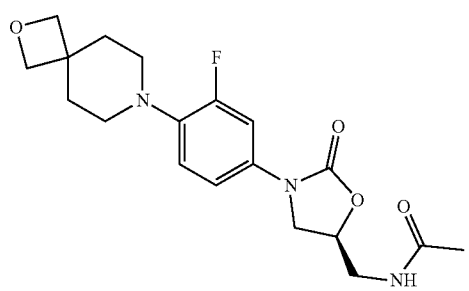 [SMILES: CC(=O)NC[C@H]1CN(c2ccc(N3CCC4(CC3)COC4)c(F)c2)C(=O)O1]

Prepared by following similar procedure as described for example 6 using appropriate modifications. $^1$H NMR (CDCl$_3$): 7.41 (dd, J=2.4 and 14.0 Hz, 1H), 7.08-7.06 (m, 1H), 6.95-6.90 (m, 1H), 5.99 (m, 1H), 4.78-4.77 (m, 1H), 4.50 (s, 4H), 4.05-4.01 (m, 1H), 3.77-3.75 (m, 2H), 3.73-3.70 (m, 1H), 2.96-2.93 (m, 4H), 2.07-2.04 (m, 7H). ESI-MS (m/z): 378.15 (M+H)$^+$

Example 8

Preparation of (S)—N-((3-(3,5-difluoro-4-(4-(oxetan-3-yl)piperidin-1-yl)phenyl)-2-oxooxazolidin-5-yl)methyl)acetamide

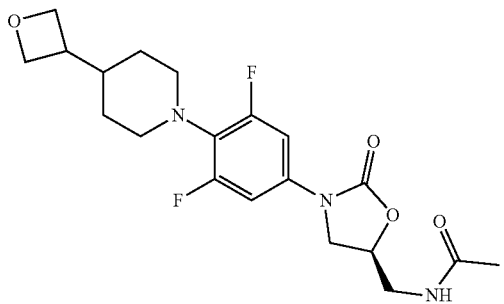 [SMILES: CC(=O)NC[C@H]1CN(c2cc(F)c(N3CCC(C4COC4)CC3)c(F)c2)C(=O)O1]

Step 1: (R)-2-(3-((3,5-difluoro-4-(4-(oxetan-3-yl)piperidin-1-yl)phenyl)amino)-2-hydroxypropyl)isoindoline-1,3-dione

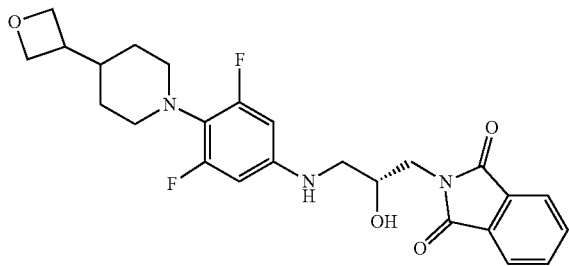 [SMILES: O=C1c2ccccc2C(=O)N1C[C@H](O)CNc1cc(F)c(N2CCC(C3COC3)CC2)c(F)c1]

A stirring solution of (S)-2-(oxiran-2-ylmethyl)isoindoline-1,3-dione (1.988 g, 9.78 mmol) and 3,5-difluoro-4-(4-(oxetan-3-yl)piperidin-1-yl)aniline (1.50 g, 5.59 mmol) in aq. EtOH was heated at 100° C. for 4 h. Another (S)-2-(oxiran-2-ylmethyl)isoindoline-1,3-dione (1.988 g, 9.78 mmol) was added at 80° C. and stirring continued for 16 h. Reaction mixture was filtered to get the title product. ESI-MS (m/z): 472.16 [M+H]$^+$.

Step 2: (S)-2-((3-(3,5-difluoro-4-(4-(oxetan-3-yl)piperidin-1-yl)phenyl)-2-oxooxazolidin-5-yl)methy)isoindoline-1,3-dione

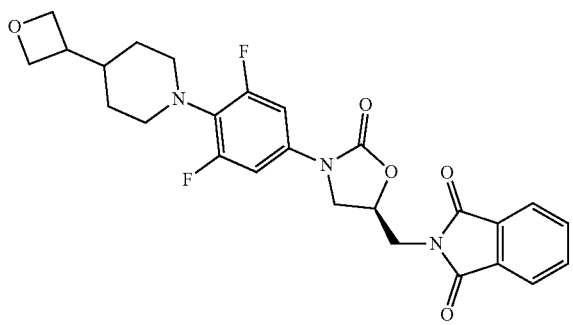 [SMILES: O=C1c2ccccc2C(=O)N1C[C@H]1CN(c2cc(F)c(N3CCC(C4COC4)CC3)c(F)c2)C(=O)O1]

To a stirring solution of product of step 1 (2.0 g, 4.24 mmol) in CHCl$_3$ was added CDI (2.75 g, 16.97 mmol) at 25-30° C. The reaction mixture was stirred at 70° C. for 5 h. Solvent was distilled out and reaction mixture was acidified by 35% hydrochloric acid to get pH=2. Product was extracted with DCM. Organic layer was separated, dried over Na$_2$SO$_4$ and distilled out to get the title product. ESI-MS (m/z): 498.14 [M+H]$^+$.

Step 3: (S)-5-(aminomethyl)-3-(3,5-difluoro-4-(4-(oxetan-3-yl)piperidin-1-yl)phenyl)oxazolidin-2-one

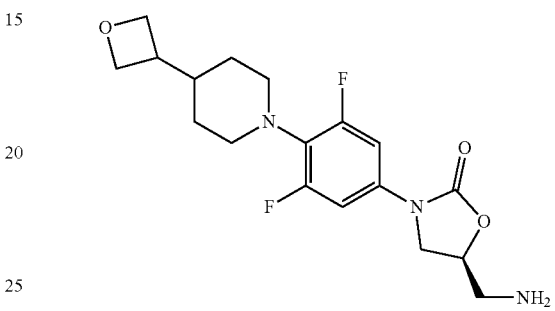

To a stirring solution of product of step 2 (1.90 g, 3.82 mmol) in EtOH was added aq. Methyl amine (2.97 g, 38.2 mmol) at 25-30° C. Reaction mixture was stirred at 80° C. for 3 h. After complete conversion of starting material, reaction mixture was diluted with DCM (100 ml) and washed with cold water. Organic layer was dried over Na$_2$SO$_4$ and distilled out to get the title product as solid. ESI-MS (m/z): 368.15 [M+H]$^+$.

Step 4: (S)—N-((3-(3,5-difluoro-4-(4-(oxetan-3-yl)piperidin-1-yl)phenyl)-2-oxooxazolidin-5-yl)methyl)acetamide

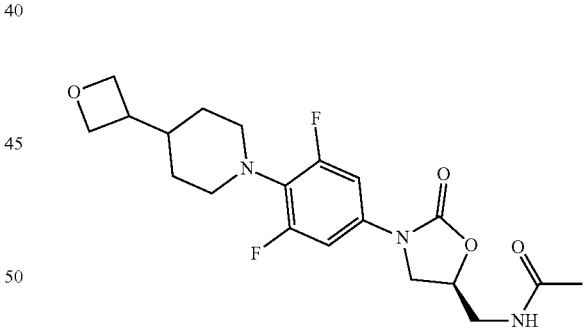

To a stirring solution of product of step 3 (1.00 g, 2.72 mmol) in DCM was added pyridine (0.330 ml, 4.08 mmol) and acetic anhydride (0.360 ml, 3.81 mmol) and stirred for 2 h at 25-30° C. After complete conversion of starting material reaction mixture was diluted with water and extracted with DCM. Organic layer was separated, dried over Na$_2$SO$_4$ and distilled out to get crude product which was purified by preparative HPLC to get title product as white solid. $^1$H NMR (DMSO): 8.23 (t, 1H), 7.28-7.21 (m, 2H), 4.75-4.69 (m, 1H), 4.63-4.60 (m, 2H), 4.38-4.35 (m, 2H), 4.10-4.05 (m, 1H), 3.70-3.66 (m,/H), 3.43-3.38 (m,/H), 3.11-2.97 (m, 4H), 2.78-2.72 (m, 1H), 1.83 (s, 3H), 1.76-1.71 (m, 1H), 1.68-1.60 (m, 2H), 1.19-1.06 (m, 2H). ESI-MS (m/z): 410.16 [M+H]$^+$.

Example 9

Preparation of (S)—N-((3-(4-(4-(1,1-dioxidothietan-3-yl)piperidin-1-3/1)-3,5-difluorophenyl)-2-oxooxazolidin-5-yl)methyl)acetamide

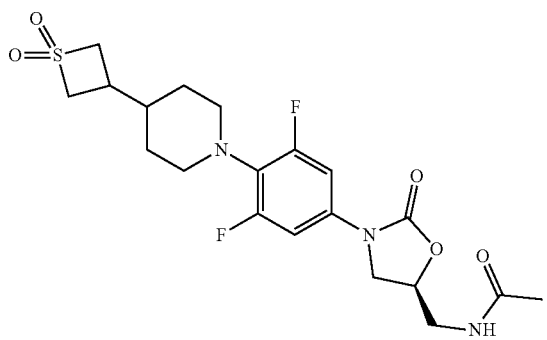 [SMILES: CC(=O)NC[C@H]1CN(c2cc(F)c(N3CCC(C4CS(=O)(=O)C4)CC3)c(F)c2)C(=O)O1]

Step 1: tert-butyl 4-oxopiperidine-1-carboxylate

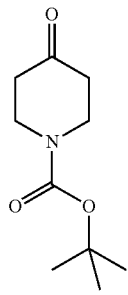

To a stirring suspension of piperidin-4-one hydrochloride (30 g, 221 mmol) in dry DCM was added TEA (83 ml, 597 mmol) followed by Di-tert-butyl dicarbonate (64.2 ml, 277 mmol) drop wise over a period of 15 min. at 10-15° C. The resulting mixture was stirred at 25-30° C. for 16 h. The reaction mixture was diluted with DCM and washed with water. The organic layer was dried over $Na_2SO_4$ and evaporated under reduced pressure to get the title product.

Step 2: diethyl 2-(1-(tert-butoxycarbonyl)piperidin-4-ylidene)malonate

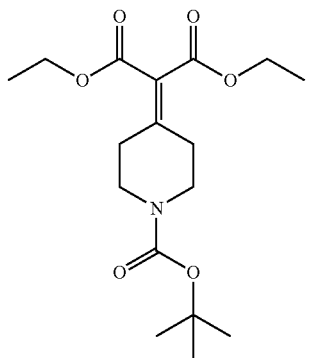 [SMILES: CCOC(=O)C(C(=O)OCC)=C1CCN(C(=O)OC(C)(C)C)CC1]

A stirring solution of $TiCl_4$ (52.0 ml, 472 mmol) in carbon tetrachloride (40 ml) was added to THF (150 mL) at 0° C. To this was added a solution of product of step 1 (37.3 g, 187 mmol) and diethyl malonate (25.7 ml, 168 mmol) in THF (150 mL) at 0° C. and stirred for 15 min. To this was added pyridine (98 ml, 1217 mmol) and stirred for 16 h at 25-30° C. Reaction mixture poured into 10% citric acid solution and product was extracted with EtOAc. Organic layer was separated, dried over $Na_2SO_4$ and evaporated under reduced pressure to get the title product.

Step 3: diethyl 2-(1-(tert-butoxycarbonyl)piperidin-4-yl)malonate

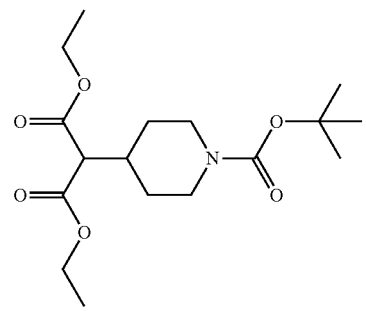 [SMILES: CCOC(=O)C(C(=O)OCC)C1CCN(C(=O)OC(C)(C)C)CC1]

To a stirring solution of product of step 2 (63 g, 185 mmol) in EtOH was added sodium borohydride (6.98 g, 185 mmol) and stirred for 2 h at 25-30° C. After complete conversion of starting material, reaction mixture was poured into ice water and extracted with DCM. Organic layer was separated, dried over $Na_2SO_4$ and evaporated under reduced pressure to get the title product.

Step 4: tert-butyl 4-(1,3-dihydroxypropan-2-yl)piperidine-1-carboxylate

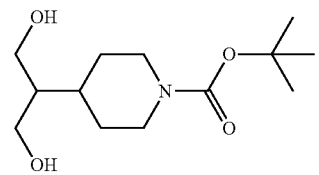 [SMILES: CC(C)(C)OC(=O)N1CCC(C(CO)CO)CC1]

To a stirring solution of product of step 3 (63 g, 183 mmol) in EtOH (315 ml) was added sodium borohydride (69.4 g, 1834 mmol) at 25-30° C. and the resulting mixture was stirred at 70° C. for 3 h. After complete conversion of starting material, reaction mixture was diluted with cold water and extracted with EtOAc. Organic layer was separated, dried over $Na_2SO_4$ and evaporated under reduced pressure to get the title product.

Step 5: tert-butyl 4-(1,3-bis(tosyloxy)propan-2-yl)piperidine-1-carboxylate

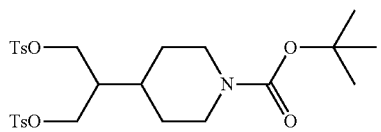

To a stirring solution of product of step 4 (10 g, 38.6 mmol) in DCM was added TEA (21.50 ml, 154 mmol) and DMAP (9.42 g, 77 mmol). To this was added portion wise p-toluene sulfonylchloride (22.05 g, 116 mmol) at 0-5° C. The reaction mixture was stirred at 25-30° C. for 3 h. After completion of reaction, reaction mixture was diluted with DCM and washed with water and brine, dried over Na₂SO₄ and evaporated under reduced pressure to get the title product.

Step 6: tert-butyl 4-(thietan-3-yl)piperidine-1-carboxylate

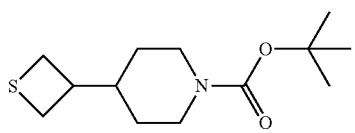 [SMILES: CC(C)(C)OC(=O)N1CCC(C2CSC2)CC1]

To a stirring solution of product of step 5 (12.1 g, 21.31 mmol) in DMF was added sodium sulfide nonahydrate (6.14 g, 25.6 mmol) and reaction mixture was heated at 80-85° C. for 16 h. After completion of reaction, it was diluted with EtOAc and water. Organic layer was separated, dried over Na₂SO₄ and concentrated to get oily product. The crude product was purified by column chromatography using Hexane/EtOAc to get the title product.

Step 7: tert-butyl 4-(1,1-dioxidothietan-3-yl)piperidine-1-carboxylate

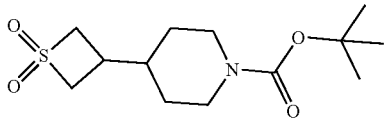 [SMILES: CC(C)(C)OC(=O)N1CCC(C2CS(=O)(=O)C2)CC1]

To a stirring solution of product of step 6 (5.5 g, 21.371 mmol) in DCM was added meta-chloroperbenzoic acid (18.44 g, 107 mmol) and stirred for 4 h at 25-30° C. After completion of reaction, it was diluted with DCM and washed with aq. NaHCO₃. DCM layer was separated, dried over Na₂SO₄ and concentrated to get the title product. ¹H NMR (CDCl₃): 4.19-3.99 (m, 4H), 3.88-3.85 (m, 2H), 2.70-2.60 (m, 2H), 2.45-2.41 (m, 1H), 2.35-2.22 (m, 1H), 1.87-1.86 (m, 2H), 1.55 (s, 9H), 1.21-1.1 (m, 2H).

Step 8: 3-(1-(2,6-difluoro-4-nitrophenyl)piperidin-4-yl)thietane 1,1-dioxide

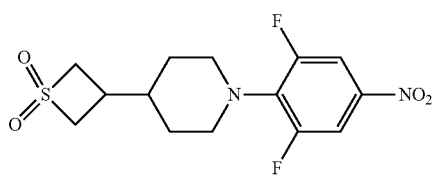 [SMILES: O=[N+]([O-])c1cc(F)c(N2CCC(C3CS(=O)(=O)C3)CC2)c(F)c1]

To a stirring solution of product of step 7 (5.5 g, 19.01 mmol) in DCM was added TFA (2.93 ml, 38.0 mmol) at 0° C. and stirred for 3 h 25-30° C. After completion of reaction, DCM was evaporated to get crude product which was diluted with DMF. To this was added K₂CO₃ (5.39 g, 39.0 mmol) and 1,2,3-trifluoro-5-nitrobenzene (2.3 g, 12.99 mmol) and stirred for 4 h at 80° C. Reaction mixture was diluted with water to get product as solid. ESI-MS (m/z): 347.07 [M+H]⁺.

Step 9: 3-(1-(4-amino-2,6-difluorophenyl)piperidin-4-yl)thietane 1,1-dioxide

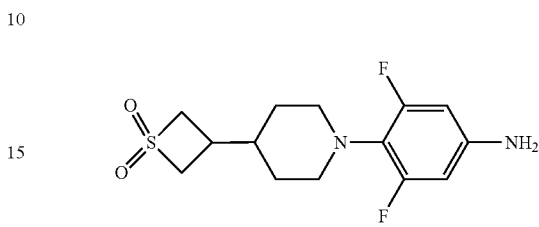

To a stirring solution of product of step 8 (2.3 g, 6.64 mmol) in THF was added Pd-C (71 mg) and stirred under hydrogen pressure for 3 h at 25-30° C. After completion of reaction, it was passed through hyflow bed and solvent was evaporated to get the title product. ESI-MS (m/z): 317.10 [M+H]⁺.

Step 10: benzyl (4-(4-(1,1-dioxidothietan-3-yl)piperidin-1-yl)-3,5-difluorophenyl)carbamate

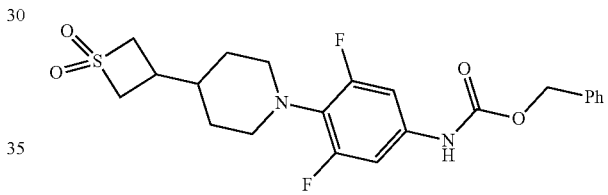

To a stirring solution of product of step 9 (2.14 g, 6.76 mmol) in THF was added NaHCO₃ (2.27 g, 27.1 mmol) and benzyl chloroformate (2.124 ml, 7.44 mmol) at 0-5° C. The reaction mixture was stirred at 25-30° C. for 7 h. After completion of reaction it was diluted with EtOAc and water. Organic layer was separated and evaporated under reduced pressure to get the crude product. The crude product was purified by column chromatography using Hexane/EtOAc to get the title product. ESI-MS (m/z): 451.10 [M+H]⁺.

Step 11: (R)-3-(4-(4-(1,1-dioxidothietan-3-yl)piperidin-1-yl)-3,5-difluorophenyl)-5-(hydroxymethyl)oxazolidin-2-one

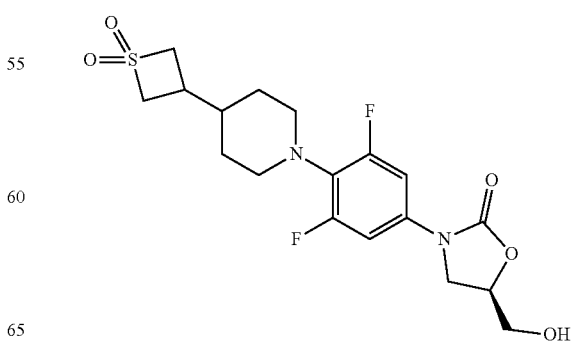

To a stirring solution of product of step 10 (2.47 g, 5.48 mmol) in dry THF was added n-butyllithium (2.41 ml, 6.03 mmol) at −78° C. The resultant light yellow solution was stirred at −78° C. for 1 h and then (R)-glycidyl butyrate (0.869 g, 6.03 mmol) was added at −70° C. dropwise. The reaction mixture was stirred for an additional 1 h at −78° C. The reaction mixture was allowed to warm to room temperature and stirred for 16 h. After completion of reaction it was poured into aq ammonium chloride solution and crude product was extracted with EtOAc which was purified by column chromatography to get the title product. ESI-MS (m/z): 439.10 [M+Na]⁺.

Step 12: (R)-(3-(4-(4-(1,1-dioxidothietan-3-yl)piperidin-1-yl)-3,5-difluorophenyl)-2-oxooxazolidin-5-yl)methyl methanesulfonate

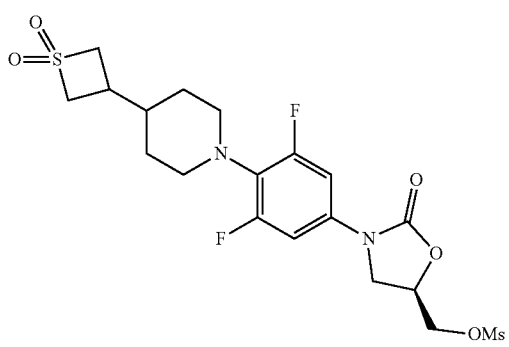 [SMILES: CS(=O)(=O)OC[C@H]1CN(c2cc(F)c(N3CCC(C4CS(=O)(=O)C4)CC3)c(F)c2)C(=O)O1]

To a stirring solution of product of step 11 (590 mg, 1.417 mmol) in DCM was added TEA (0.257 ml, 1.842 mmol) and methanesulfonyl chloride (0.116 ml, 1.488 mmol) at 0-5° C. Reaction mixture was stirred for 2 h at 25-30° C. After completion of reaction it was diluted with DCM and washed with water. DCM layer was dried over Na₂SO₄ and distilled out to get the title product. ESI-MS (m/z): 495.10 [M+H]⁺.

Step 13: (R)-5-(azidomethyl)-3-(4-(4-(1,1-dioxidothietan-3-yl)piperidin-1-yl)-3,5-difluorophenyl)oxazolidin-2-one

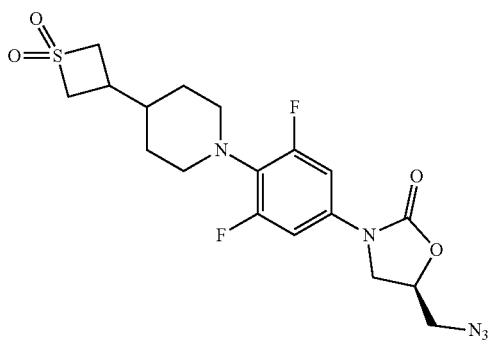 [SMILES: [N-]=[N+]=NC[C@H]1CN(c2cc(F)c(N3CCC(C4CS(=O)(=O)C4)CC3)c(F)c2)C(=O)O1]

To a stirring solution of product of step 12 (650 mg, 1.314 mmol) in DMF was added sodium azide (427 mg, 6.57 mmol) and stirred for 3 h at 60-65° C. After completion of reaction it was diluted with water and filtered to get the title product. ESI-MS (m/z): 442.17 [M+H]⁺.

Step 14: (S)-5-(aminomethyl)-3-(4-(4-(1,1-dioxidothietan-3-yl)piperidin-1-yl)-3,5-difluorophenyl)oxazolidin-2-one

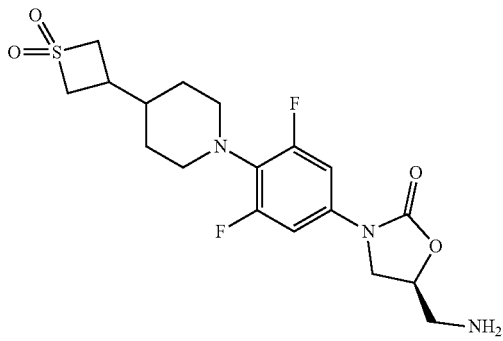 [SMILES: NC[C@H]1CN(c2cc(F)c(N3CCC(C4CS(=O)(=O)C4)CC3)c(F)c2)C(=O)O1]

To a stirring solution of product of step 13 (500 mg, 1.133 mmol) in MeOH was added Pd-C(12 mg) at 0-5° C. To this was added sodium borohydride (129 mg, 3.40 mmol) portion wise and stirred for 3 h at 25-30° C. After completion of reaction it was passed through hyflow bed and washed with EtOAc (50 ml). Organic layer was dried over Na₂SO₄ and concentrated to get the title product. ESI-MS (m/z): 416.15 [M+H]⁺.

Step 15: (S)—N-((3-(4-(4-(1,1-dioxidothietan-3-yl)piperidin-1-yl)-3,5-difluorophenyl)-2-oxooxazolidin-5-yl)methyl)acetamide

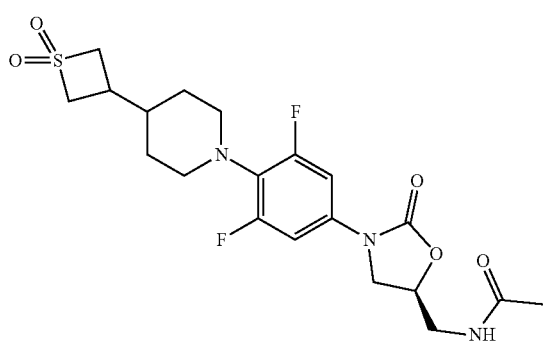 [SMILES: CC(=O)NC[C@H]1CN(c2cc(F)c(N3CCC(C4CS(=O)(=O)C4)CC3)c(F)c2)C(=O)O1]

To a stirring solution of product of step 14 (200 mg, 0.481 mmol) in DCM (5 ml) was added pyridine (0.058 ml, 0.722 mmol), and acetic anhydride (0.064 ml, 0.674 mmol). Reaction mixture was stirred for 1 h at 25-30° C. After completion of reaction, it was diluted with DCM and washed with water. Organic layer was dried over Na₂SO₄ and concentrated to get the title product. ¹H NMR (DMSO-d₆): 8.23 (t, J=5.8 Hz, 1H), 7.28-7.23 (m, 2H), 4.74-4.70 (m, 1H), 4.19-4.15 (m, 2H), 4.13-1.05 (m, 1H), 4.01-3.96 (m, 2H), 3.70-3.66 (m, 1H), 3.41-3.39 (m, 2H), 3.12-3.10 (m, 2H), 2.99-2.94 (m, 2H), 2.30-2.27 (m, 1H), 1.83 (s, 3H), 1.71-1.68 (m, 2H), 1.57-1.54 (m, 1H), 1.27-1.21 (m, 2H). ESI-MS (m/z): 458.18 (M+H)⁺

Example 10

Preparation of (S)—N-((3-(4-(4-(1,1-dioxidothietan-3-yl)piperidin-1-yl)-3-fluorophenyl)-2-oxooxazolidin-5-yl)methyl)acetamide

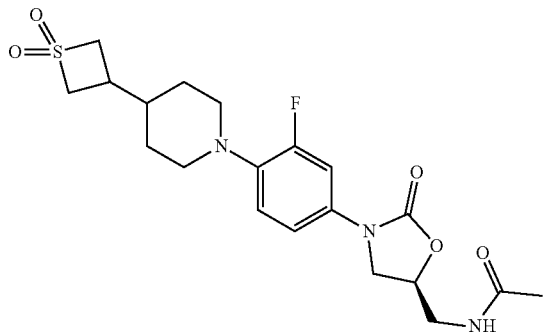 [SMILES: CC(=O)NC[C@H]1CN(c2ccc(N3CCC(C4CS(=O)(=O)C4)CC3)c(F)c2)C(=O)O1]

Prepared by following similar procedure as described for example 9 using appropriate modifications. $^1$H NMR (DMSO-d$_6$): 8.24 (t, 1H), 7.44 (dd, J=2.4 and 14.8 Hz, 1H), 7.16-7.14 (m, 1H), 7.09-7.06 (m, 1H), 4.72 (m, 1H), 4.20-4.10 (m, 2H), 4.07-4.02 (m, 1H), 4.01-3.97 (m, 2H), 3.71-3.67 (m, 1H), 3.40 (t, 2H), 3.29 (bs, 2H), 2.62-2.59 (m, 2H), 2.35-2.28 (m, 1H), 1.83 (s, 3H), 1.70-1.82 (m, 2H), 1.51-1.62 (m, 1H), 1.23-1.34 (m, 2H). ESI-MS (m/z): 440.12 (M+H)$^+$.

Example 11

Preparation of methyl (S)-((3-(4-(4-(1,1-dioxidothietan-3-yl)piperidin-1-yl)-3,5-difluorophenyl)-2-oxooxazolidin-5-yl)methyl)carbamate

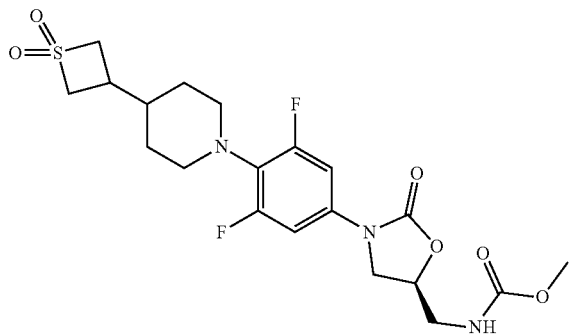 [SMILES: COC(=O)NC[C@H]1CN(c2cc(F)c(N3CCC(C4CS(=O)(=O)C4)CC3)c(F)c2)C(=O)O1]

To a stirring solution of (S)-5-(aminomethyl)-3-(4-(4-(1,1-dioxidothietan-3-yl)piperidin-1-yl)-3,5-difluorophenyl)oxazolidin-2-one (100 mg, 0.241 mmol) in DCM was added pyridine (0.029 ml, 0.361 mmol) and methyl chloroformate (0.026 ml, 0.337 mmol). Reaction mixture was stirred for 1 h at 25-30° C. After completion of reaction, it was diluted with DCM Organic layer was separated, dried over Na$_2$SO$_4$ and concentrated to get the title product. $^1$H NMR (CDCl$_3$): 7.53 (t, 1H), 7.50 (d, J=5.6 Hz, 2H), 4.73-4.70 (m, 1H), 4.19-4.15 (m, 2H), 4.13-4.10 (m, 1H), 4.08-3.96 (m, 2H), 3.74-3.70 (m, 1H), 3.54 (s, 3H), 3.12-3.00 (m, 2H), 2.97-2.94 (m, 2H), 2.30-2.26 (m, 1H), 1.71-1.68 (m, 2H), 1.57-1.55 (m, 1H), 1.24-1.21 (m, 4H). ESI-MS (m/z): 474.151 (M+H)$^+$.

Using appropriate starting materials and suitable modifications of the process described in above examples, including suitable addition and/or deletion of steps as may be necessary, well within the scope of a person skilled in the art the following compounds were prepared in an analogues manner

TABLE 1

| EX. No. | IUPAC Name | ESI-MS (m/z) (M + H)$^+$ |
|---|---|---|
| 12 | (S)-N-((3-(4-(2,2-dioxido-2-thia-7-azaspiro[3.5]nonan-7-yl)-3,5-difluorophenyl)-2-oxooxazolidin-5-yl)methyl)thiophene-2-carboxamide | 512.17 |
| 13 | (S)-N-((3-(4-(2,2-dioxido-2-thia-7-azaspiro[3.5]nonan-7-yl)-3-fluorophenyl)-2-oxooxazolidin-5-yl)methyl)thiophene-2-carboxamide | 494.15 |
| 14 | (S)-N-((3-(4-(2,2-dioxido-2-thia-7-azaspiro[3.5]nonan-7-yl)-3,5-difluorophenyl)-2-oxooxazolidin-5-yl)methyl)furan-2-carboxamide | 496.12 |
| 15 | (S)-N-((3-(4-(2,2-dioxido-2-thia-7-azaspiro[3.5]nonan-7-yl)-3-fluorophenyl)-2-oxooxazolidin-5-yl)methyl)furan-2-carboxamide | 478.15 |
| 16 | (S)-N-((3-(4-(4-(1,1-dioxidothietan-3-yl)piperidin-1-yl)-3,5-difluorophenyl)-2-oxooxazolidin-5-yl)methyl)thiophene-2-carboxamide | 526.13 |
| 17 | (S)-N-((3-(4-(4-(1,1-dioxidothietan-3-yl)piperidin-1-yl)-3-fluorophenyl)-2-oxooxazolidin-5-yl)methyl)thiophene-2-carboxamide | 508.16 |
| 18 | (S)-N-((3-(4-(4-(1,1-dioxidothietan-3-yl)piperidin-1-yl)-3,5-difluorophenyl)-2-oxooxazolidin-5-yl)methyl)furan-2-carboxamide | 510.17 |
| 19 | (S)-N-((3-(4-(4-(1,1-dioxidothietan-3-yl)piperidin-1-yl)-3-fluorophenyl)-2-oxooxazolidin-5-yl)methyl)furan-2-carboxamide | 492.11 |
| 20 | (S)-N-((3-(4-(2,2-dioxido-2-thia-7-azaspiro[3.5]nonan-7-yl)-3,5-difluorophenyl)-2-oxooxazolidin-5-yl)methyl)butyramide | 472.14 |
| 21 | (S)-N-((3-(4-(2,2-dioxido-2-thia-7-azaspiro[3.5]nonan-7-yl)-3-fluorophenyl)-2-oxooxazolidin-5-yl)methyl)butyramide | 544.2 |
| 22 | (S)-N-((3-(4-(4-(1,1-dioxidothietan-3-yl)piperidin-1-yl)-3,5-difluorophenyl)-2-oxooxazolidin-5-yl)methyl)butyramide | 486.14 |
| 23 | (S)-N-((3-(4-(4-(1,1-dioxidothietan-3-yl)piperidin-1-yl)-3-fluorophenyl)-2-oxooxazolidin-5-yl)methyl)butyramide | 468.16 |
| 24 | ethyl (S)-((3-(4-(2,2-dioxido-2-thia-7-azaspiro[3.5]nonan-7-yl)-3,5-difluorophenyl)-2-oxooxazolidin-5-yl)methyl)carbamate | 474.15 |
| 25 | ethyl (S)-((3-(4-(2,2-dioxido-2-thia-7-azaspiro[3.5]nonan-7-y1)-3-fluorophenyl)-2-oxooxazolidin-5-yl)methyl)carbamate | 456.13 |
| 26 | ethyl (S)-((3-(4-(4-(1,1-dioxidothietan-3-yl)piperidin-1-yl)-3,5-difluorophenyl)-2-oxooxazolidin-5-yl)methyl)carbamate | 488.14 |
| 27 | ethyl (S)-((3-(4-(4-(1,1-dioxidothietan-3-yl)piperidin-1-yl)-3-fluorophenyl)-2-oxooxazolidin-5-yl)methyl)carbamate | 470.16 |
| 28 | (S)-N-((3-(4-(2,2-dioxido-2-thia-7-azaspiro[3.5]nonan-7-yl)-3,5-difluorophenyl)-2-oxooxazolidin-5-yl)methyl)cyclopropanecarboxamide | 470.12 |
| 29 | (S)-N-((3-(4-(2,2-dioxido-2-thia-7-azaspiro[3.5]nonan-7-yl)-3-fluorophenyl)-2-oxooxazolidin-5-yl)methyl)cyclopropanecarboxamide | 452.14 |
| 30 | (S)-N-((3-(4-(4-(1,1-dioxidothietan-3-yl)piperidin-1-yl)-3,5-difluorophenyl)-2-oxooxazolidin-5-yl)methyl)cyclopropanecarboxamide | 484.18 |
| 31 | (S)-N-((3-(4-(4-(1,1-dioxidothietan-3-yl)piperidin-1-yl)-3-fluorophenyl)-2-oxooxazolidin-5-yl)methyl)cyclopropanecarboxamide | 466.15 |
| 32 | (S)-N-((3-(4-(2,2-dioxido-2-thia-7-azaspiro[3.5]nonan-7-yl)-3,5-difluorophenyl)-2-oxooxazolidin-5-yl)methyl)cyclobutanecarboxamide | 484.18 |
| 33 | (S)-N-((3-(4-(2,2-dioxido-2-thia-7-azaspiro[3.5]nonan-7-yl)-3-fluorophenyl)-2-oxooxazolidin-5-yl)methyl)cyclobutanecarboxamide | 466.15 |

TABLE 1-continued

| EX. No. | IUPAC Name | ESI-MS (m/z) (M + H)+ |
|---|---|---|
| 34 | (S)-N-((3-(4-(4-(1,1-dioxidothietan-3-yl)piperidin-1-yl)-3,5-difluorophenyl)-2-oxooxazolidin-5-yl)methyl)cyclobutanecarboxamide | 498.16 |
| 35 | (S)-N-((3-(4-(4-(1,1-dioxidothietan-3-yl)piperidin-1-yl)-3-fluorophenyl)-2-oxooxazolidin-5-yl)methyl)cyclobutanecarboxamide | 480.2 |
| 36 | (R)-5-((1H-1,2,3-triazol-1-yl)methyl)-3-(4-(2,2-dioxido-2-thia-7-azaspiro[3.5]nonan-7-yl)-3-fluorophenyl)oxazolidin-2-one | 436.12 |
| 37 | (R)-5-((1H-1,2,3-triazol-1-yl)methyl)-3-(4-(4-(1,1-dioxidothietan-3-yl)piperidin-1-yl)-3,5-difluorophenyl)oxazolidin-2-one | 468.13 |
| 38 | (R)-5-((1H-1,2,3-triazol-1-yl)methyl)-3-(4-(4-(1,1-dioxidothietan-3-yl)piperidin-1-yl)-3-fluorophenyl)oxazolidin-2-one | 450.14 |
| 39 | (R)-5-((1H-1,2,4-triazol-1-yl)methyl)-3-(4-(2,2-dioxido-2-thia-7-azaspiro[3.5]nonan-7-yl)-3,5-difluorophenyl)oxazolidin-2-one | 454.12 |
| 40 | (R)-5-((1H-1,2,4-triazol-1-yl)methyl)-3-(4-(2,2-dioxido-2-thia-7-azaspiro[3.5]nonan-7-yl)-3-fluorophenyl)oxazolidin-2-one | 436.12 |
| 41 | (S)-3-(4-(2,2-dioxido-2-thia-7-azaspiro[3.5]nonan-7-yl)-3-fluorophenyl)-5-((isoxazol-3-ylamino)methyl)oxazolidin-2-one | 451.12 |
| 42 | (S)-3-(4-(4-(1,1-dioxidothietan-3-yl)piperidin-1-yl)-3,5-difluorophenyl)-5-((isoxazol-3-ylamino)methyl)oxazolidin-2-one | 483.16 |
| 43 | methyl (S)-((3-(4-(4-(1,1-dioxidothietan-3-yl)piperidin-1-yl)-3-fluorophenyl)-2-oxooxazolidin-5-yl)methyl)carbamate | 456.18 |
| 44 | methyl (S)-((3-(4-(2,2-dioxido-2-thia-7-azaspiro[3.5]nonan-7-yl)-3-fluorophenyl)-2-oxooxazolidin-5-yl)methyl)carbamate | 442.15 |
| 45 | methyl (S)-((3-(3-fluoro-4-(2-oxa-7-azaspiro[3.5]nonan-7-yl)phenyl)-2-oxooxazolidin-5-yl)methyl)carbamate | 394.11 |
| 46 | (R)-5-((1H-1,2,3-triazol-1-yl)methyl)-3-(3-fluoro-4-(2-oxa-7-azaspiro[3.5]nonan-7-yl)phenyl)oxazolidin-2-one | 388.18 |
| 47 | methyl (S)-((3-(3,5-difluoro-4-(2-oxa-7-azaspiro[3.5]nonan-7-yl)phenyl)-2-oxooxazolidin-5-yl)methyl)carbamate | 412.14 |
| 48 | (R)-5-((1H-1,2,3-triazol-1-yl)methyl)-3-(3,5-difluoro-4-(2-oxa-7-azaspiro[3.5]nonan-7-yl)phenyl)oxazolidin-2-one | 406.15 |
| 49 | (R)-5-((1H-1,2,3-triazol-1-yl)methyl)-3-(3,5-difluoro-4-(4-(oxetan-3-yl)piperidin-1-yl)phenyl)oxazolidin-2-one | 420.17 |

Biological Evaluation:

Minimum Inhibitory Concentration (MIC) Determination

To assess the bacterial growth inhibitory effect of the compounds of the invention, MABA assay was performed with log phase culture of *Mycobacterium tuberculosis* H37Rv. Bacterial culture of optical density 0.6-0.8 was diluted to final density of 0.02 in 7H9 medium. 1000 of diluted *Mycobacterium tuberculosis* H37Rv was incubated with the test compounds in microtiter plate. A drug free control containing DMSO also was also prepared. Following incubation of the compound with culture for 7 days at 37° C., 20 μl of 0.02% alamar blue (freshly prepared) was added in each well. The color was allowed to develop for 16 h at 37° C. Blue color in the well indicated no growth whereas pink color signifies growth in the well. MIC value is defined as the lowest concentration that prevents the color change from blue to pink. Fluorescence was measured at excitation at 530 nm and emission at 590 nm. MIC values of the selected compounds are shown in Table 2.

TABLE 2

| Example | Mtb MIC (μM) |
|---|---|
| 1 | 1.25 |
| 2 | 1.25 |
| 3 | 1.25 |
| 4 | 1.25 |
| 5 | 1.25 |
| 6 | 1.25-2.5 |
| 7 | 2.5 |
| 8 | 2.5 |
| 9 | 1.25 |
| 10 | 2.5 |

The novel compounds of the present invention can be formulated into suitable pharmaceutically acceptable compositions by combining with suitable excipients by techniques and processes and concentrations as are well known. Pharmaceutical composition comprising the compounds of the present invention may comprise a suitable binder, suitable bulking agent &/or diluent and any other suitable agents as may be necessary.

Novel compounds of the present invention can be used for the treatment of mammalian infections such as tuberculosis by administrating therapeutically active and non-toxic amount of compounds of formula (I) or pharmaceutically acceptable compositions thereof.

A method of treating anti-tuberculosis infection in a subject that comprising administering to a patient in need thereof an effective amount of a compound of formula (I) or its suitable pharmaceutical composition.

The pharmaceutical compositions according to this invention can exist in various forms. In some embodiments, the pharmaceutical composition is in the topical, oral or parenteral administration.

One or more additional pharmaceutical agents or treatment methods can be used in combination with the compounds of the present invention for treatment or prevention of mammalian infection. The therapeutic agents can be combined with the present compounds in a single dosage form, or the agents can be administered simultaneously or sequentially in separate dosage forms. The compound of formula (I) can be administered in combination with other therapeutic agents such as isoniazide, rifampin, rifapentine, rifabutin, ethambutol, pyrazinamide, streptomycin, amikacin, levofloxacin, ofloxacin, p-aminosalicylic acid.

While the present invention has been described in terms of its specific embodiments, certain modifications and equivalents will be apparent to those skilled in the art and are intended to be included within the scope of the present invention.

The invention claimed is:

1. A compound of general formula (I),

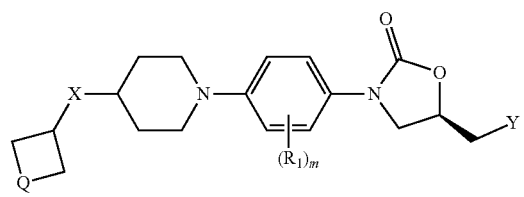

Formula (I)

or a pharmaceutically acceptable salt thereof, wherein, X is either absent or a bond;

whenever X is absent, the four membered ring is directly attached to the 6-membered piperidine ring forming spirocyclic system with the spiro carbon at position 4 of the piperidine ring and Q being beta to the spiro carbon; Q is either O or S(O)p; p=0-2 integer; Y is OH, NR2R3, or NHC(O)R4; R1 is selected from H, F, Cl, CH3, CN and OCH3; m=1-4 integer; R2 and R3 are independently selected from H, (C1-C6)alkyl, (C3-C6)cycloalkyl, aryl, heterocyclyl and heteroaryl each of which may be further optionally substituted; or Rz and R3 are taken together with the nitrogen to which they are attached to form a 4- to 8-membered heterocyclyl or heteroaryl with 1 to 3 additional heteroatoms selected from O, S, or N, which heterocyclyl or heteroaryl may be further be optionally substituted; R4 is independently selected from (C1-C6)alkyl, (C3-C6)cycloalkyl, aryl, heteroaryl and (C1-C6)alkoxy, each of which is optionally substituted; substitutions are selected from halo, hydroxyl, (C1-C6)alkyl, (C1-C6)alkoxy, (C1-C6) acyloxy, haloalkyl, NO2, CN and NH2.

2. The compound of formula (I) or salt thereof as claimed in claim 1 wherein the $(C_1-C_6)$alkyl group of $R_2$, $R_3$ and $R_4$ is selected from methyl, ethyl, n-propyl, and iso-propyl; the $(C_1-C_6)$alkoxy group of $R_2$, $R_3$ and $R_4$ is selected from methoxy and ethoxy; and the $(C_3-C_6)$cycloalkyl group of $R_2$, $R_3$ and $R_4$ is selected from cyclopropyl and cyclobutyl.

3. The compound of formula (I) or salt thereof as claimed in claim 1 wherein heteroaryl group of $R_4$ is selected from thienyl, furyl, isoxazolyl, and triazolyl.

4. The compound of formula (I) or salt thereof as claimed in claim 1 wherein the compound is selected from
(R)-5-((1H-1,2,3-triazol-1-yl)methyl)-3-(4-(2,2-dioxido-2-thia-7-azaspiro[3.5]nonan-7-yl)-3,5-difluorophenyl)oxazolidin-2-one;
(S)-3-(4-(2,2-dioxido-2-thia-7-azaspiro[3.5]nonan-7-yl)-3,5-difluorophenyl)-5-((isoxazol-3-ylamino)methyl)oxazolidin-2-one;
(S)—N-((3-(4-(2,2-dioxido-2-thia-7-azaspiro[3.5]nonan-7-yl)-3,5-difluorophenyl)-2-oxooxazolidin-5-yl)methyl)acetamide;
(S)-methyl ((3-(4-(2,2-dioxido-2-thia-7-azaspiro[3.5]nonan-7-yl)-3,5-difluorophenyl)-2-oxooxazolidin-5-yl)methyl)carbamate;
(S)—N-((3-(4-(2,2-dioxido-2-thia-7-azaspiro[3.5]nonan-7-yl)-3-fluorophenyl)-2-oxooxazolidin-5-yl)methyl)acetamide;
(S)—N-((3-(3,5-difluoro-4-(2-oxa-7-azaspiro[3.5]nonan-7-yl)phenyl)-2-oxooxazolidin-5-yl)methyl)acetamide;
(S)—N-((3-(3-fluoro-4-(2-oxa-7-azaspiro[3.5]nonan-7-yl)phenyl)-2-oxooxazolidin-5-yl)methyl)acetamide;
(S)—N-((3-(3,5-difluoro-4-(4-(oxetan-3-yl)piperidin-1-yl)phenyl)-2-oxooxazolidin-5-yl)methyl)acetamide;
(S)—N-((3-(4-(4-(1,1-dioxidothietan-3-yl)piperidin-1-yl)-3,5-difluorophenyl)-2-oxooxazolidin-5-yl)methyl)acetamide;
(S)—N-((3-(4-(4-(1,1-dioxidothietan-3-yl)piperidin-1-yl)-3-fluorophenyl)-2-oxooxazolidin-5-yl)methyl)acetamide;
methyl (S)-((3-(4-(4-(1,1-dioxidothietan-3-yl)piperidin-1-yl)-3,5-difluorophenyl)-2-oxooxazolidin-5-yl)methyl)carbamate;
(S)-5-(aminomethyl)-3-(4-(4-(1,1-dioxidothietan-3-yl)piperidin-1-yl)-3,5-difluorophenyl)oxazolidin-2-one;
(R)-3-(4-(4-(1,1-dioxidothietan-3-yl)piperidin-1-yl)-3,5-difluorophenyl)-5-(hydroxymethyl)oxazolidin-2-one;
(S)-5-(aminomethyl)-3-(3,5-difluoro-4-(4-(oxetan-3-yl)piperidin-1-yl)phenyl)oxazolidin-2-one;
(S)-5-(aminomethyl)-3-(3,5-difluoro-4-(2-oxa-7-azaspiro[3.5]nonan-7-yl)phenyl)oxazolidin-2-one;
(S)-5-(aminomethyl)-3-(4-(2,2-dioxido-2-thia-7-azaspiro[3.5]nonan-7-yl)-3,5-difluorophenyl)oxazolidin-2-one;
(R)-3-(4-(2,2-dioxido-2-thia-7-azaspiro[3.5]nonan-7-yl)-3,5-difluorophenyl)-5-(hydroxymethyl)oxazolidin-2-one;
(S)—N-((3-(4-(2,2-dioxido-2-thia-7-azaspiro[3,5]nonan-7-yl)-3,5-difluorophenyl)-2-oxooxazolidin-5-yl)methyl)thiophene-2-carboxamide;
(S)—N-((3-(4-(2,2-dioxido-2-thia-7-azaspiro[3.5]nonan-7-yl)-3-fluorophenyl)-2-oxooxazolidin-5-yl)methyl)thiophene-2-carboxamide;
(S)—N-((3-(4-(2,2-dioxido-2-thia-7-azaspiro[3.5]nonan-7-yl)-3,5-difluorophenyl)-2-oxooxazolidin-5-yl)methyl)furan-2-carboxamide;
(S)—N-((3-(4-(2,2-dioxido-2-thia-7-azaspiro[3.5]nonan-7-yl)-3-fluorophenyl)-2-oxooxazolidin-5-yl)methyl)furan-2-carboxamide;
(S)—N-((3-(4-(4-(1,1-dioxidothietan-3-yl)piperidin-1-yl)-3,5-difluorophenyl)-2-oxooxazolidin-5-yl)methyl)thiophene-2-carboxamide;
(S)—N-((3-(4-(4-(1,1-dioxidothietan-3-yl)piperidin-1-yl)-3-fluorophenyl)-2-oxooxazolidin-5-yl)methyl)thiophene-2-carboxamide;
(S)—N-((3-(4-(4-(1,1-dioxidothietan-3-yl)piperidin-1-yl)-3,5-difluorophenyl)-2-oxooxazolidin-5-yl)methyl)furan-2-carboxamide;
(S)—N-((3-(4-(4-(1,1-dioxidothietan-3-yl)piperidin-1-yl)-3-fluorophenyl)-2-oxooxazolidin-5-yl)methyl)furan-2-carboxamide;
(S)—N-((3-(4-(2,2-dioxido-2-thia-7-azaspiro[3.5]nonan-7-yl)-3,5-difluorophenyl)-2-oxooxazolidin-5-yl)methyl)butyramide;
(S)—N-((3-(4-(2,2-dioxido-2-thia-7-azaspiro[3.5]nonan-7-yl)-3-fluorophenyl)-2-oxooxazolidin-5-yl)methyl)butyramide;
(S)—N-((3-(4-(4-(1,1-dioxidothietan-3-yl)piperidin-1-yl)-3,5-difluorophenyl)-2-oxooxazolidin-5-yl)methyl)butyramide;
(S)—N-((3-(4-(4-(1,1-dioxidothietan-3-yl)piperidin-1-yl)-3-fluorophenyl)-2-oxooxazolidin-5-yl)methyl)butyramide;
ethyl (S)-((3-(4-(2,2-dioxido-2-thia-7-azaspiro[3.5]nonan-7-yl)-3,5-difluorophenyl)-2-oxooxazolidin-5-yl)methyl)carbamate;
ethyl (S)-((3-(4-(2,2-dioxido-2-thia-7-azaspiro[3.5]nonan-7-yl)-3-fluorophenyl)-2-oxooxazolidin-5-yl)methyl)carbamate;
ethyl (S)-((3-(4-(4-(1,1-dioxidothietan-3-yl)piperidin-1-yl)-3,5-difluorophenyl)-2-oxooxazolidin-5-yl)methyl)carbamate;
ethyl (S)-((3-(4-(4-(1,1-dioxidothietan-3-yl)piperidin-1-yl)-3-fluorophenyl)-2-oxooxazolidin-5-yl)methyl)carbamate;
(xazolidin-5-yl)methyl)cyclobutanecarboxamide;
(R)-5-((1H-1,2,3-triazol-1-yl)methyl)-3-(4-(2,2-dioxido-2-thia-7-azaspiro[3.5]nonan-7-yl)-3-fluorophenyl)oxazolidin-2-one;
(R)-5-((1H-1,2,3-triazol-1-yl)methyl)-3-(4-(4-(1,1-dioxidothietan-3-yl)piperidin-1-yl)-3,5-difluorophenyl)oxazolidin-2-one;
(R)-5-((1H-1,2,3-triazol-1-yl)methyl)-3-(4-(4-(1,1-dioxidothietan-3-yl)piperidin-1-yl)-3-fluorophenyl)oxazolidin-2-one;

(R)-5-((1H-1,2,4-triazol-1-yl)methyl)-3-(4-(2,2-dioxido-2-thia-7-azaspiro[3.5]nonan-7-yl)-3,5-difluorophenyl)oxazolidin-2-one;

(R)-5-((1H-1,2,4-triazol-1-yl)methyl)-3-(4-(2,2-dioxido-2-thia-7-azaspiro[3.5]nonan-7-yl)-3-fluorophenyl)oxazolidin-2-one;

(S)-3-(4-(2,2-dioxido-2-thia-7-azaspiro[3.5]nonan-7-yl)-3-fluorophenyl)-5-((isoxazol-3-ylamino)methyl)oxazolidin-2-one;

(S)-3-(4-(4-(1,1-dioxidothietan-3-yl)piperidin-1-yl)-3,5-difluorophenyl)-5-((isoxazol-3-ylamino)methyl)oxazolidin-2-one;

methyl (S)-((3-(4-(4-(1,1-dioxidothietan-3-yl)piperidin-1-yl)-3-fluorophenyl)-2-oxooxazolidin-5-yl)methyl)carbamate;

methyl (S)-((3-(4-(2,2-dioxido-2-thia-7-azaspiro[3.5]nonan-7-yl)-3-fluorophenyl)-2-oxooxazolidin-5-yl)methyl)carbamate;

methyl (S)-((3-(3-fluoro-4-(2-oxa-7-azaspiro[3.5]nonan-7-yl)phenyl)-2-oxooxazolidin-5-yl)methyl)carbamate;

(R)-5-((1H-1,2,3-triazol-1-yl)methyl)-3-(3-fluoro-4-(2-oxa-7-azaspiro[3.5]nonan-7-yl)phenyl)oxazolidin-2-one;

methyl (S)-((3-(3,5-difluoro-4-(2-oxa-7-azaspiro[3.5]nonan-7-yl)phenyl)-2-oxooxazolidin-5-yl)methyl)carbamate;

(R)-5-((1H-1,2,3-triazol-1-yl)methyl)-3-(3,5-difluoro-4-(2-oxa-7-azaspiro[3.5]nonan-7-yl)phenyl)oxazolidin-2-one; and (R)-5-((1H-1,2,3-triazol-1-yl)methyl)-3-(3,5-difluoro-4-(4-(oxetan-3-yl)piperidin-1-yl)phenyl)oxazolidin-2-one.

5. A pharmaceutical composition comprising a therapeutically effective amount of a compound of formula (I) or salt thereof as claimed in claim 1 and optionally one or more pharmaceutically acceptable carriers, diluents or excipients.

6. A method of treating a tuberculosis infection in a patient comprising administering an effective amount of a compound of formula (I) as claimed in claim 1 or salt thereof or a pharmaceutical composition comprising a compound or salt of claim 1 to the patient.

* * * * *